(12) United States Patent
Saiki et al.

(10) Patent No.: US 10,539,560 B2
(45) Date of Patent: Jan. 21, 2020

(54) SUBSTRATE FOR SAMPLE ANALYSIS, AND SAMPLE ANALYSIS APPARATUS

(71) Applicant: PHC HOLDINGS CORPORATION, Tokyo (JP)

(72) Inventors: Masayuki Saiki, Ehime (JP); Masahiro Johno, Ehime (JP); Fusatoshi Okamoto, Ehime (JP); Kazuya Kondoh, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 437 days.

(21) Appl. No.: 15/323,001

(22) PCT Filed: Jun. 29, 2015

(86) PCT No.: PCT/JP2015/068729
§ 371 (c)(1),
(2) Date: Dec. 29, 2016

(87) PCT Pub. No.: WO2016/002731
PCT Pub. Date: Jan. 7, 2016

(65) Prior Publication Data
US 2017/0168046 A1    Jun. 15, 2017

(30) Foreign Application Priority Data

Jun. 30, 2014 (JP) .................. 2014-134776
Jun. 30, 2014 (JP) .................. 2014-134777

(51) Int. Cl.
*G01N 1/00* (2006.01)
*G01N 33/543* (2006.01)
*B01L 3/00* (2006.01)

(52) U.S. Cl.
CPC ........ *G01N 33/54366* (2013.01); *B01L 3/502* (2013.01); *G01N 33/54326* (2013.01);
(Continued)

(58) Field of Classification Search
CPC ...................................................... G01N 1/00
See application file for complete search history.

(56) References Cited

U.S. PATENT DOCUMENTS

| 4,495,295 A | 1/1985 | Neurath |
| 4,673,653 A | 6/1987 | Guigan |

(Continued)

FOREIGN PATENT DOCUMENTS

| EP | 0326100 A2 | 8/1989 |
| EP | 0724156 A1 | 7/1996 |

(Continued)

OTHER PUBLICATIONS

Extended European Search Report dated Dec. 21, 2017, issued in counterpart European Patent Application No. 15814780.1.

(Continued)

*Primary Examiner* — Jyoti Nagpaul
(74) *Attorney, Agent, or Firm* — McDermott Will & Emery LLP

(57) ABSTRACT

A substrate for sample analysis is a substrate for sample analysis used for causing a binding reaction between an analyte and a ligand in a liquid sample, the substrate for sample analysis including: a base substrate having a rotation axis and a predetermined thickness; a chamber located in the base substrate for holding a liquid sample containing an analyte and a ligand immobilized on a surface of magnetic particles; and at least one magnet arranged at a position such that the magnetic particles are captured in the chamber by the magnet.

15 Claims, 19 Drawing Sheets

(52) U.S. Cl.
CPC ............... *B01L 2300/0627* (2013.01); *B01L 2400/0409* (2013.01)

(56) References Cited

U.S. PATENT DOCUMENTS

| | | | |
|---|---|---|---|
| 4,745,077 A | 5/1988 | Holian et al. | |
| 4,916,081 A | 4/1990 | Kamada et al. | |
| 4,918,025 A | 4/1990 | Grenner | |
| 4,990,075 A | 2/1991 | Wogoman | |
| 5,160,702 A | 11/1992 | Kopf-Sill et al. | |
| 5,173,262 A * | 12/1992 | Burtis ............... | B01L 3/502753 422/50 |
| 5,466,574 A | 11/1995 | Liberti et al. | |
| 5,627,041 A | 5/1997 | Shartle | |
| 5,741,714 A | 4/1998 | Liberti | |
| 5,912,134 A | 6/1999 | Shartle | |
| 6,063,589 A | 5/2000 | Kellogg et al. | |
| 6,103,537 A | 8/2000 | Ullman et al. | |
| 6,238,538 B1 | 5/2001 | Parce et al. | |
| 6,274,384 B1 | 8/2001 | Starzl et al. | |
| 6,458,553 B1 | 10/2002 | Colin et al. | |
| 6,551,841 B1 | 4/2003 | Wilding et al. | |
| 7,476,543 B2 | 1/2009 | Becker et al. | |
| 7,867,753 B2 | 1/2011 | Andersson | |
| 7,897,398 B2 | 3/2011 | Saiki | |
| 8,058,010 B2 | 11/2011 | Erickson et al. | |
| 8,415,140 B2 | 4/2013 | Saiki et al. | |
| 8,703,070 B1 | 4/2014 | Parng et al. | |
| 8,956,879 B2 | 2/2015 | Tanaka et al. | |
| 2002/0019059 A1 | 2/2002 | Chow et al. | |
| 2002/0071788 A1 | 6/2002 | Fujii et al. | |
| 2002/0119482 A1 | 8/2002 | Nelson et al. | |
| 2002/0137218 A1 | 9/2002 | Mian et al. | |
| 2002/0151078 A1 | 10/2002 | Kellogg et al. | |
| 2002/0180975 A1 | 12/2002 | Ogura et al. | |
| 2003/0026740 A1 | 2/2003 | Staats | |
| 2003/0077204 A1 | 4/2003 | Seki et al. | |
| 2003/0138819 A1 | 7/2003 | Gong et al. | |
| 2003/0211010 A1 | 11/2003 | Nagaoka et al. | |
| 2004/0089616 A1 | 5/2004 | Kellogg et al. | |
| 2004/0137607 A1 | 7/2004 | Tanaami et al. | |
| 2004/0181343 A1 | 9/2004 | Wigstrom et al. | |
| 2005/0079634 A1 | 4/2005 | Wilding et al. | |
| 2005/0123447 A1 | 6/2005 | Koike et al. | |
| 2005/0178218 A1 | 8/2005 | Montagu | |
| 2005/0221281 A1 | 10/2005 | Ho | |
| 2005/0287577 A1 | 12/2005 | Yamamichi | |
| 2006/0061760 A1 | 3/2006 | Matsumoto et al. | |
| 2006/0263242 A1 | 11/2006 | Yang et al. | |
| 2006/0292641 A1 | 12/2006 | Nakanishi et al. | |
| 2007/0141576 A1 | 6/2007 | Koide | |
| 2007/0160979 A1 | 7/2007 | Andersson | |
| 2007/0166721 A1 | 7/2007 | Phan et al. | |
| 2007/0189927 A1 | 8/2007 | Ballhorn et al. | |
| 2007/0218566 A1 | 9/2007 | Barten et al. | |
| 2007/0224304 A1 | 9/2007 | Kunimatsu et al. | |
| 2007/0243111 A1 | 10/2007 | Momose | |
| 2007/0266777 A1 | 11/2007 | Bergman et al. | |
| 2008/0035579 A1 | 2/2008 | Lee et al. | |
| 2008/0073546 A1 | 3/2008 | Andersson et al. | |
| 2008/0102537 A1 | 5/2008 | Harding et al. | |
| 2008/0131978 A1 | 6/2008 | Fujimura et al. | |
| 2008/0138831 A1 | 6/2008 | Hataoka | |
| 2008/0156079 A1 | 7/2008 | Momose | |
| 2008/0171400 A1 | 7/2008 | Cho et al. | |
| 2008/0176272 A1 | 7/2008 | Bergman et al. | |
| 2008/0219891 A1 | 9/2008 | McDevitt et al. | |
| 2008/0240996 A1 | 10/2008 | Harding et al. | |
| 2008/0242556 A1 | 10/2008 | Cao et al. | |
| 2009/0042317 A1 | 2/2009 | Ikeda | |
| 2009/0053108 A1 | 2/2009 | Cho et al. | |
| 2009/0111190 A1 | 4/2009 | Andersson et al. | |
| 2009/0123337 A1 | 5/2009 | Noda et al. | |
| 2009/0126516 A1 | 5/2009 | Yamamoto et al. | |
| 2009/0155125 A1 | 6/2009 | Michiue et al. | |
| 2009/0169430 A1 | 7/2009 | Yamamoto et al. | |
| 2009/0253130 A1 | 10/2009 | Yoo | |
| 2009/0317896 A1 | 12/2009 | Yoo | |
| 2010/0071486 A1 | 3/2010 | Kim et al. | |
| 2010/0074801 A1 | 3/2010 | Saiki | |
| 2010/0078322 A1 | 4/2010 | Yamanishi et al. | |
| 2010/0132820 A1 | 6/2010 | Ozaki et al. | |
| 2010/0151560 A1 | 6/2010 | Wo et al. | |
| 2010/0159600 A1 | 6/2010 | Shin et al. | |
| 2010/0184228 A1 | 7/2010 | Saiki | |
| 2010/0221741 A1 | 9/2010 | Saiki et al. | |
| 2010/0255589 A1 * | 10/2010 | Saiki ............... | G01N 33/02 436/45 |
| 2010/0262389 A1 | 10/2010 | Nakanishi et al. | |
| 2010/0281961 A1 | 11/2010 | Saiki et al. | |
| 2010/0290955 A1 | 11/2010 | Cho et al. | |
| 2011/0045505 A1 | 2/2011 | Warthoe et al. | |
| 2011/0058985 A1 | 3/2011 | Saiki et al. | |
| 2011/0117665 A1 | 5/2011 | Saiki et al. | |
| 2011/0124128 A1 | 5/2011 | Oosterbroek et al. | |
| 2011/0126646 A1 | 6/2011 | Saiki et al. | |
| 2011/0250695 A1 | 10/2011 | Sarofim et al. | |
| 2012/0024083 A1 | 2/2012 | Wo et al. | |
| 2012/0135533 A1 | 5/2012 | Shikida et al. | |
| 2012/0244607 A1 | 9/2012 | Iwamoto et al. | |
| 2012/0261256 A1 | 10/2012 | Chang et al. | |
| 2012/0269701 A1 | 10/2012 | Linder et al. | |
| 2012/0275971 A1 | 11/2012 | Momose | |
| 2012/0322683 A1 | 12/2012 | Liu et al. | |
| 2013/0029361 A1 | 1/2013 | Hamachi et al. | |
| 2013/0074962 A1 | 3/2013 | Garcia da Fonseca et al. | |
| 2013/0142697 A1 | 6/2013 | Kim et al. | |
| 2013/0164763 A1 | 6/2013 | Saiki et al. | |
| 2013/0206701 A1 | 8/2013 | Strohmeier et al. | |
| 2013/0260481 A1 | 10/2013 | Shimizu et al. | |
| 2013/0261010 A1 | 10/2013 | Bailey et al. | |
| 2013/0266956 A1 | 10/2013 | Tia et al. | |
| 2013/0288351 A1 | 10/2013 | Nitta | |
| 2014/0004505 A1 | 1/2014 | Su et al. | |
| 2014/0073041 A1 | 3/2014 | Kijima | |
| 2014/0234184 A1 | 8/2014 | Oshika et al. | |
| 2014/0242721 A1 | 8/2014 | Kellogg et al. | |
| 2014/0270459 A1 | 9/2014 | Moll et al. | |
| 2014/0273192 A1 | 9/2014 | Sharpe et al. | |
| 2015/0087544 A1 | 3/2015 | Putnam et al. | |
| 2015/0093771 A1 | 4/2015 | Griss et al. | |
| 2015/0098864 A1 | 4/2015 | Yang | |
| 2015/0111778 A1 | 4/2015 | McDevitt et al. | |
| 2015/0251183 A1 | 9/2015 | Saiki | |
| 2015/0355132 A1 | 12/2015 | Crooks et al. | |
| 2017/0131304 A1 | 5/2017 | Johno et al. | |
| 2017/0131305 A1 | 5/2017 | Okamoto et al. | |
| 2017/0138972 A1 | 5/2017 | Johno et al. | |
| 2017/0350910 A1 | 12/2017 | Okamoto et al. | |

FOREIGN PATENT DOCUMENTS

| | | |
|---|---|---|
| EP | 0871539 A1 | 10/1998 |
| EP | 1105457 A1 | 6/2001 |
| EP | 2072134 A2 | 6/2009 |
| EP | 2133150 A1 | 12/2009 |
| EP | 2 175 278 A1 | 4/2010 |
| EP | 2253958 A1 | 11/2010 |
| EP | 2311565 A1 | 4/2011 |
| EP | 2402460 A1 | 1/2012 |
| EP | 2602025 A1 | 6/2013 |
| JP | S60-159651 A | 8/1985 |
| JP | S61-264263 A | 11/1986 |
| JP | H01-227061 A | 9/1989 |
| JP | H05-297001 A | 11/1993 |
| JP | H05-322894 A | 12/1993 |
| JP | H07-500910 A | 1/1995 |
| JP | H08-262024 A | 10/1996 |
| JP | H09-218201 A | 8/1997 |
| JP | H09-257796 A | 10/1997 |
| JP | H09-325148 A | 12/1997 |
| JP | H10-300752 A | 11/1998 |
| JP | 2001-502793 A | 2/2001 |
| JP | 2002-236131 A | 8/2002 |

(56) References Cited

FOREIGN PATENT DOCUMENTS

| | | |
|---|---|---|
| JP | 2003-043052 A | 2/2003 |
| JP | 2004-163104 A | 6/2004 |
| JP | 2005-010031 A | 1/2005 |
| JP | 2005-345160 A | 12/2005 |
| JP | 2006-010535 A | 1/2006 |
| JP | 2006-068384 A | 3/2006 |
| JP | 2006-112824 A | 4/2006 |
| JP | 2006-177850 A | 7/2006 |
| JP | 2006-258696 A | 9/2006 |
| JP | 2007-003361 A | 1/2007 |
| JP | 2007-003414 A | 1/2007 |
| JP | 2007-010341 A | 1/2007 |
| JP | 2007-024851 A | 2/2007 |
| JP | 2007-047031 A | 2/2007 |
| JP | 2007-064742 A | 3/2007 |
| JP | 2007-071557 A | 3/2007 |
| JP | 2007-071655 A | 3/2007 |
| JP | 2007-078676 A | 3/2007 |
| JP | 2007-101240 A | 4/2007 |
| JP | 2007-279069 A | 10/2007 |
| JP | 2007-285792 A | 11/2007 |
| JP | 2007-530938 A | 11/2007 |
| JP | 2007-315879 A | 12/2007 |
| JP | 2008-064701 A | 3/2008 |
| JP | 2008-064748 A | 3/2008 |
| JP | 2008-128906 A | 6/2008 |
| JP | 2008-134126 A | 6/2008 |
| JP | 2008-157708 A | 7/2008 |
| JP | 2008-164360 A | 7/2008 |
| JP | 2008-164434 A | 7/2008 |
| JP | 2008-216237 A | 9/2008 |
| JP | 2009-014529 A | 1/2009 |
| JP | 2009-031116 A | 2/2009 |
| JP | 2009-042104 A | 2/2009 |
| JP | 2009-109251 A | 5/2009 |
| JP | 2009-121860 A | 6/2009 |
| JP | 2009-128342 A | 6/2009 |
| JP | 2009-133831 A | 6/2009 |
| JP | 2009-139289 A | 6/2009 |
| JP | 2009-156717 A | 7/2009 |
| JP | 2009-156778 A | 7/2009 |
| JP | 2009-162701 A | 7/2009 |
| JP | 2009-180688 A | 8/2009 |
| JP | 2009-180697 A | 8/2009 |
| JP | 2009-186296 A | 8/2009 |
| JP | 2009-210564 A | 9/2009 |
| JP | 2009-287971 A | 12/2009 |
| JP | 2010-071644 A | 4/2010 |
| JP | 2010-122022 A | 6/2010 |
| JP | 2010-151447 A | 7/2010 |
| JP | 2010-210531 A | 9/2010 |
| JP | 2010-243373 A | 10/2010 |
| JP | 2010-286297 A | 12/2010 |
| JP | 2011-007778 A | 1/2011 |
| JP | 2011-069618 A | 4/2011 |
| JP | 2011-183589 A | 9/2011 |
| JP | 2011-196849 A | 10/2011 |
| JP | 2012-143204 A | 8/2012 |
| JP | 2012-159325 A | 8/2012 |
| JP | 2012-215515 A | 11/2012 |
| JP | 2012-229985 A | 11/2012 |
| JP | 2013-050435 A | 3/2013 |
| JP | 2013-079812 A | 5/2013 |
| JP | 2013-205305 A | 10/2013 |
| JP | 2014-032018 A | 2/2014 |
| JP | 2014-044077 A | 3/2014 |
| JP | 2014-048209 A | 3/2014 |
| JP | 2014-106207 A | 6/2014 |
| JP | 2014-190906 A | 10/2014 |
| JP | 2014-232023 A | 12/2014 |
| JP | 2015-121493 A | 7/2015 |
| JP | 2015-197338 A | 11/2015 |
| JP | 2015-223562 A | 12/2015 |
| WO | 90/013016 A1 | 11/1990 |
| WO | 90/015321 A2 | 12/1990 |
| WO | 92/016844 A1 | 10/1992 |
| WO | 93/08893 A1 | 5/1993 |
| WO | 96/026011 A1 | 8/1996 |
| WO | 98/13684 A1 | 4/1998 |
| WO | 1999/064836 A1 | 12/1999 |
| WO | 01/087485 A2 | 11/2001 |
| WO | 02/23163 A1 | 3/2002 |
| WO | 05/075997 A1 | 8/2005 |
| WO | 2007/005077 A1 | 1/2007 |
| WO | 2007/105584 A1 | 9/2007 |
| WO | 2007/116909 A1 | 10/2007 |
| WO | 07/122943 A1 | 11/2007 |
| WO | 2008/053743 A1 | 5/2008 |
| WO | 2008/139697 A1 | 11/2008 |
| WO | 2010/044598 A2 | 4/2010 |
| WO | 10/058303 A1 | 5/2010 |
| WO | 2010/077159 A1 | 7/2010 |
| WO | 2012/164552 A1 | 12/2012 |
| WO | 2014/017018 A1 | 1/2014 |

OTHER PUBLICATIONS

International Search Report issued in corresponding International Patent Application No. PCT/JP2015/068729, dated Sep. 1, 2015; with English translation.
International Search Report issued in corresponding International Patent Application No. PCT/JP2015/068724, dated Sep. 1, 2015; with English translation.
International Search Report issued in corresponding International Patent Application No. PCT/JP2015/068723, dated Sep. 29, 2015; with English translation.
International Search Report issued in corresponding International Patent Application No. PCT/JP2015/068722, dated Sep. 29, 2015; with English translation.
Non-Final Office Action issued in related U.S. Appl. No. 15/323,007, dated Jan. 4, 2019.
Chinese Search Report issued in corresponding Chinese Patent Application No. 201580035558.6, dated Dec. 15, 2017; with partial English translation.
Final Office Action issued in related U.S. Appl. No. 15/323,007, dated May 16, 2019.
International Search Report issued in International Patent Application No. PCT/JP2015/084738, dated Mar. 15, 2016; with English translation.
Extended European Search Report issued in European Patent Application No. 15866519.0, dated Jun. 19, 2018.
Notice of Allowance issued in related U.S. Appl. No. 15/322,977, dated Sep. 11, 2019.
Notice of Allowance issued in related U.S. Appl. No. 15/322,910, dated Feb. 25, 2019.

* cited by examiner

SUBSTRATE FOR SAMPLE ANALYSIS, AND SAMPLE ANALYSIS APPARATUS

RELATED APPLICATIONS

This application is the U.S. National Phase under 35 U.S.C. § 371 of International Patent Application No. PCT/JP2015/068729, filed on Jun. 29, 2015, which in turn claims the benefit of Japanese Application No. 2014-134776, filed on Jun. 30, 2014 and Japanese Application No. 2014-134777, filed on Jun. 30, 2014, the disclosures of which Applications are incorporated by reference herein.

TECHNICAL FIELD

The present application relates to a substrate for sample analysis and a sample analysis device.

BACKGROUND ART

Patent Document No. 1 discloses a technique for analyzing a particular component of an analyte such as urine or blood.

More specifically, Patent Document No. 1 discloses a technique for analyzing a specific component in an analyte by rotating a disc-shaped substrate for sample analysis having channels, chambers, etc., formed therein, so as to, for example, transfer, distribute and mix the liquid inside the substrate.

CITATION LIST

Patent Literature

[Patent Document No. 1] Japanese National Phase PCT Laid-Open Publication No. 7-500910

SUMMARY OF INVENTION

Technical Problem

There has been a demand for techniques, other than that described in Patent Document No. 1, that are capable of accommodating various analyzing methods.

A non-limiting example embodiment of the present application provides a substrate for sample analysis and a sample analysis device capable of accommodating various analyzing methods.

Solution to Problem

A substrate for sample analysis is a substrate for sample analysis used for causing a binding reaction between an analyte and a ligand in a liquid sample, the substrate for sample analysis including: a base substrate having a rotation axis and a predetermined thickness; a chamber located in the base substrate for holding a liquid sample containing an analyte and a ligand immobilized on a surface of magnetic particles; and at least one magnet arranged at a position such that the magnetic particles are captured in the chamber by the magnet.

Advantageous Effects of Invention

A substrate for sample analysis and a sample analysis device according to one embodiment of the present application are capable of accommodating various analysis methods with a simple configuration.

BRIEF DESCRIPTION OF DRAWINGS

FIG. 5 An example diagram showing an example configuration of the sample analysis device 1 for optically detecting the magnet 16a.

FIG. 7 An example graph showing an output result of a photodetection device 26a.

FIG. 8 An example diagram showing an example configuration of the sample analysis device 1 for detecting the presence/absence of a magnetic force of the magnet 16a.

FIG. 14A An example top view showing the base substrate 110a.

FIG. 14B An example cross-sectional view showing the base substrate 110a.

DESCRIPTION OF EMBODIMENTS

A known method for analyzing components of an analyte, such as urine or blood, uses a binding reaction between an analyte being the subject for analysis and a ligand which specifically binds to the analyte. Examples of such assay techniques include immunoassay techniques and genetic diagnosis techniques.

Example immunoassay techniques include those using magnetic particles (referred to also as "magnetic beads", and the like). Immunoassay techniques include competitive assays methods and non-competitive assays. Example genetic diagnosis methods include those in which gene detection is done through hybridization using magnetic particles.

Figure 17:
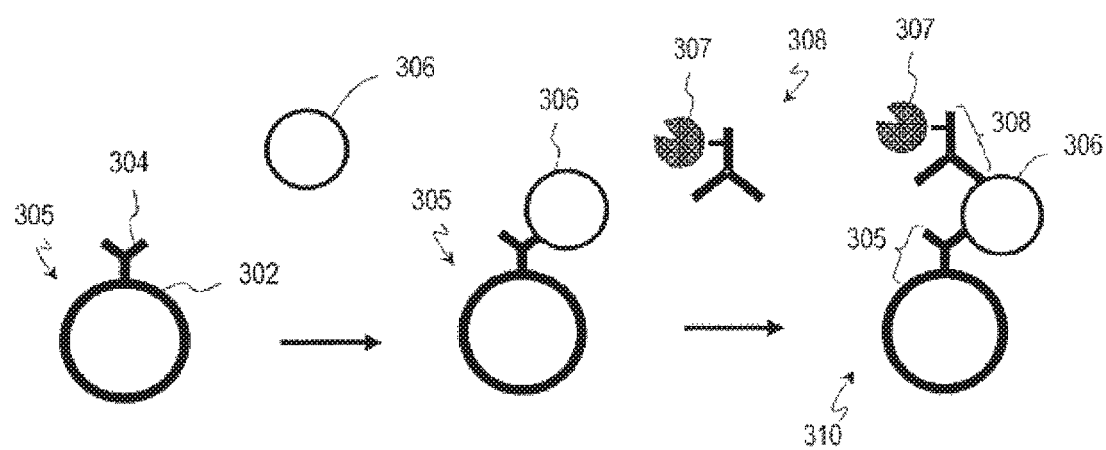
FIG. 17 An example schematic diagram illustrating a sandwich immunoassay method using magnetic particles 302.

A sandwich immunoassay (non-competitive assay) using magnetic particles will now be described in detail with reference to FIG. 17. FIG. 17 schematically shows a sandwich immunoassay using magnetic particles. The description proceeds from left to right in FIG. 17.

First, a magnetic particle immobilized antibody 305 and an antigen 306 are provided. The magnetic particle immobilized antibody 305 is an antibody 304 immobilized on the surface of a magnetic particle 302. The antibody 304 functions as a primary antibody. When an antigen-antibody reaction is allowed to occur between the magnetic particle immobilized antibody 305 and the antigen 306 (an object to be measured), there is obtained the magnetic particle immobilized antibody 305 with the antigen 306 bound thereto.

Moreover, a labeled antibody 308 is provided. The labeled antibody 308 is an antibody with a labeling substance 307 bound thereto, and functions as a secondary antibody.

When an antigen-antibody reaction is allowed to occur between the labeled antibody 308 and the antigen 306, there is obtained a complex 310 including the magnetic particle immobilized antibody 305 and the labeled antibody 308 bound to the antigen 306.

Then, a signal is detected via the labeling substance 307 of the labeled antibody 308 bound to the complex 310, thereby measuring the concentration of the antigen 306 based on the amount of signal detected. Examples of the labeling substance 307 include enzymes (e.g., peroxidase, alkaline phosphatase, luciferase), chemiluminescent substances, electrochemiluminescent substances, fluorescent substances, etc. A signal (dye, light emission or fluorescent emission) in accordance with the labeling substance used can be detected.

Antigen-antibody reaction requires a B/F separation (Bound/Free Separation) step of separating the reaction product and the unreacted substance from each other. As used herein, the "reaction product" is the complex 310, and the "unreacted substance" is, for example, an unreacted substance in the analyte, a substance adsorbed nonspecifically on a magnetic particle, or the like, or the labeled antibody 308 that was not involved in the production of the complex.

Specifically, the B/F separation step includes the step of capturing the magnetic particles 302 using a magnet, separating the reaction product and the unreacted substance from each other by removing liquids (an analyte solution, a reagent solution, a cleaning liquid, etc.) and washing the magnetic particles, and removing the unreacted substance. In order to achieve B/F separation, a magnet needs to be provided either on the side of the sample analysis device or the side of the substrate for sample analysis. The B/F separation using a magnet and magnetic particles is needed not only in non-competitive assays, but also in immunoassay techniques based on competitive assays and in gene detection methods using hybridization.

On the other hand, there is recently a demand for a technique that allows a single piece of equipment to accommodate a plurality of analyzing methods. For example, a piece of equipment capable of accommodating both an analyzing method that requires B/F separation and an analyzing method that does not require B/F separation is useful. As a more specific example, a single piece of equipment is useful, which is capable of accommodating an analyzing method based on an enzymatic colorimetric method or immunonephelometry that does not require B/F separation using a magnet, and an analyzing method that requires B/F separation using magnetic particles. Note however that such a piece of equipment will need independent elements for these analyzing methods.

On the other hand, this problem can be solved by providing a magnet on the side of the substrate for sample analysis. However, if a magnet is provided in a disposable-type substrate for sample analysis, whose demand is increasing recently, the magnet is wastefully disposed of after a single analysis.

The present inventors made an in-depth study on a technique for solving these problems, arriving at a novel substrate for sample analysis and a novel sample analysis device to be set forth below. Substrates for sample analysis and sample analysis devices according to one embodiment of the present application are listed below.

[Item 1] A substrate for sample analysis used for causing a binding reaction between an analyte and a ligand in a liquid sample, the substrate for sample analysis including:

a base substrate having a rotation axis and a predetermined thickness;

a chamber located in the base substrate and configured to hold a liquid sample containing an analyte and a ligand immobilized on a surface of magnetic particles; and at least one magnet arranged at a position where the magnetic particles are captured in the chamber by the magnet.

[Item 2] The substrate for sample analysis according to item 1, wherein the at least one magnet is provided at a position in the vicinity of a bottom surface of the chamber.

[Item 3] The substrate for sample analysis according to item 1, wherein:

the at least one magnet is provided at a position in the vicinity of a wall surface of the chamber of the base substrate; and the wall surface is a surface whose normal extends in a direction in which a centrifugal force due to rotation is exerted.

[Item 4] The substrate for sample analysis according to item 1, wherein:
the at least one magnet is provided at a position in the vicinity of a wall surface of the chamber of the base substrate; and
the wall surface is a surface on one side where the liquid sample is supported against a centrifugal force due to rotation.

[Item 5] The substrate for sample analysis according to item 1, wherein the at least one magnet is able to be attached/detached to/from the base substrate.

[Item 6] The substrate for sample analysis according to item 5, wherein:
the base substrate includes an upper surface and a lower surface; and
the at least one magnet is attached at the upper surface so as to be detachable off the upper surface.

[Item 7] The substrate for sample analysis according to item 6, wherein the base substrate includes an accommodating chamber in the upper surface for accommodating the at least one magnet.

[Item 8] The substrate for sample analysis according to item 6, wherein with the at least one magnet attached to the base substrate, the at least one magnet is projecting from the upper surface.

[Item 9] The substrate for sample analysis according to item 5, wherein:
the at least one magnet is provided in a magnet unit; and
the at least one magnet is attached/detached to/from the base substrate as the magnet unit is attached/detached to/from the base substrate.

[Item 10] The substrate for sample analysis according to item 9, wherein the magnet unit is able to be attached/detached via a lower surface of the base substrate.

[Item 11] The substrate for sample analysis according to item 9, wherein with the magnet unit attached to the base substrate, the at least one magnet is arranged at a position in the vicinity of the chamber.

[Item 12] The substrate for sample analysis according to item 9, wherein the base substrate includes an accommodating chamber for accommodating the at least one magnet when the magnet unit is attached to the base substrate.

[Item 13] The substrate for sample analysis according to any one of items 1 to 12, wherein the at least one magnet is a plurality of magnets.

[Item 14] The substrate for sample analysis according to any one of items 1 to 13, further including a balancer for making a center of gravity of the substrate generally coincide with the rotation axis when the at least one magnet is attached.

[Item 15] The substrate for sample analysis according to item 14, wherein the balancer is a non-magnet.

[Item 16] The substrate for sample analysis according to item 14 or 15, wherein the balancer is able to be attached/detached.

[Item 17] The substrate for sample analysis according to item 14, wherein the at least one magnet and the balancer can be physically distinguished from each other.

[Item 18] A sample analysis device capable of rotating the substrate for sample analysis according to any one of items 1 to 17, the sample analysis device including:
a motor that rotates the substrate for sample analysis;
a driver circuit that drives the motor; and
a detection mechanism that detects whether or not the at least one magnet is attached by using at least one of a weight of the substrate for sample analysis, a magnetic characteristic thereof, an optical characteristic thereof, a current value or a voltage value in accordance with a rotational load thereof, a rotational acceleration thereof and a steady rotation speed thereof.

[Item 19] The sample analysis device according to item 18, wherein further including a signal generation circuit that generates a signal notifying of a detection result when the detection mechanism detects that the at least one magnet is not attached.

[Item 20] The sample analysis device according to item 19, wherein the signal generation circuit generates a signal for outputting a sound, light or an image.

[Item 21] The sample analysis device according to item 18, wherein a rotation axis has an angle of 0° or more and 90° or less with respect to a direction of gravity.

[Item 22] A substrate for sample analysis used for causing a binding reaction between an analyte and a ligand in a liquid sample, the substrate for sample analysis including:
a base substrate having a rotation axis and a predetermined thickness;
a first chamber located in the base substrate and having a first space for holding a liquid sample containing an analyte and a ligand immobilized on a surface of magnetic particles;
a second chamber located in the base substrate, the second chamber arranged farther away from the rotation axis than the first chamber, and the second chamber having a second space for holding a liquid sample containing an analyte and a ligand immobilized on a surface of magnetic particles;
a first channel connecting between the first chamber and the second chamber; and
at least one magnet arranged at a position such that the magnetic particles in the second chamber are captured in the second chamber by the magnet.

[Item 23] The substrate for sample analysis according to item 22, wherein the first channel is a channel having a capillary tube for transferring a liquid by virtue of capillary action.

[Item 24] The substrate for sample analysis according to item 23, wherein when the capillary tube is filled with the liquid sample and when a centrifugal force due to rotation about the rotation axis is greater than a capillary force, the first channel transfers the liquid sample between the first chamber and the second chamber by using a siphon principle.

[Item 25] The substrate for sample analysis according to item 22, wherein the first channel is a channel capable of transferring the liquid sample by using gravity when the substrate is supported with the rotation axis being in the range of greater than 0° and 90° or less with respect to the vertical direction.

[Item 26] The substrate for sample analysis according to any one of items 22 to 25, wherein:
a third chamber located in the base substrate for holding the liquid sample, the third chamber arranged farther away from the rotation axis than the second chamber; and
a second channel connecting between the second chamber and the third chamber.

[Item 27] The substrate for sample analysis according to item 26, wherein the second channel is a channel having a capillary tube for transferring a liquid by virtue of capillary action.

[Item 28] The substrate for sample analysis according to item 27, wherein when the capillary tube is filled with the liquid sample and when a centrifugal force due to rotation about the rotation axis is greater than a capillary force, the second channel transfers the liquid sample between the first chamber and the second chamber by using a siphon principle.

[Item 29] The substrate for sample analysis according to any one of items 22 to 28, wherein the at least one magnet is provided at a position in the vicinity of a bottom surface of the second chamber.

[Item 30] The substrate for sample analysis according to any one of items 22 to 28, wherein:

the at least one magnet is provided at a position in the vicinity of a wall surface of the second chamber; and the wall surface is a surface whose normal extends in a direction in which a centrifugal force due to rotation is exerted.

[Item 31] The substrate for sample analysis according to any one of items 22 to 28, wherein:

the at least one magnet is provided at a position in the vicinity of a wall surface of the second chamber; and the wall surface is a surface on one side where the liquid sample is supported against a centrifugal force due to rotation.

[Item 32] The substrate for sample analysis according to any one of items 22 to 31, wherein the at least one magnet is able to be attached/detached to/from the base substrate.

A substrate for sample analysis and a sample analysis device in one aspect of the embodiment of the present application will now be described with reference to the accompanying drawings.

Embodiment 1

Figure 1A:
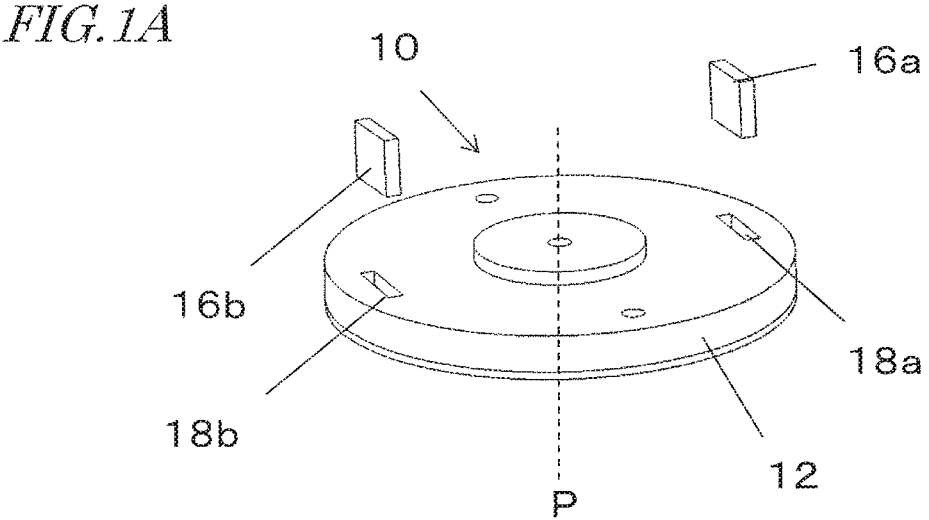
FIG. 1A An example view showing the external appearance of a substrate 10 for sample analysis.
Figure 1B:
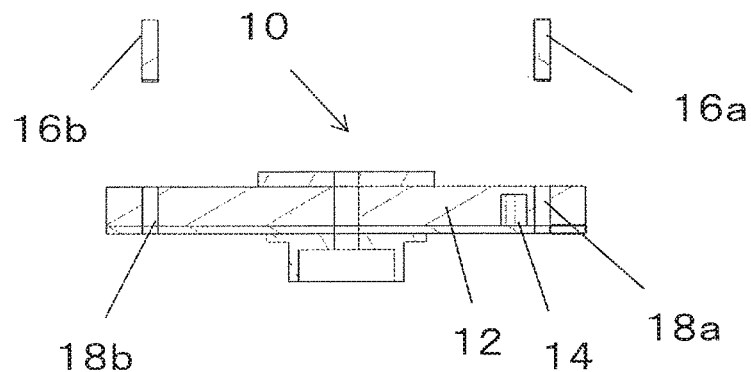
FIG. 1B An example cross-sectional view showing the substrate 10 for sample analysis.

FIG. 1A shows the external appearance of a substrate 10 for sample analysis. FIG. 1B shows a cross section of the substrate 10 for sample analysis. In the following description, the surface of the substrate 10 for sample analysis shown in FIG. 1A will be referred to as the "upper surface", the opposite surface from the upper surface as the "lower surface", and the other surface extending between the upper surface and the lower surface as the "side surface".

In the embodiment, it is assumed that the upper surface and the lower surface are each a surface to which the normal extends in parallel to the rotation axis P thereof. That is, it is assumed that the upper surface and the lower surface are perpendicular to the rotation axis P and parallel to each other. However, the upper surface and the lower surface do not need to extend parallel to each other across the entire area thereof. They may be locally or generally non-parallel to each other. At least one of the upper surface and the lower surface may include depressed portions or protruding portions. For the sake of discussion, one side of the substrate 10 for sample analysis will be referred to as the "upper surface" and the other side thereof as the "lower surface". Note that FIG. 1B shows a cross section of the substrate 10 for sample analysis taken along a plane including the rotation axis P.

The substrate 10 for sample analysis generally has a disc shape. For example, the substrate 10 for sample analysis, with a liquid having been injected into the inside thereof, is set in a sample analysis device to be described below. The sample analysis device transfers, distributes and mixes the liquid in the substrate 10 for sample analysis by rotating the substrate 10 for sample analysis. Then, the sample analysis device stops the rotation of the substrate 10 for sample analysis, for example, and optically analyzes the mixed liquid. The rotation axis P of the substrate 10 for sample analysis shown in FIG. 1A is the center of rotation about which the sample analysis device rotates the substrate 10 for sample analysis. Note that the substrate 10 for sample analysis is supported and rotated while the rotation axis P is in the range of 0° or more and 90° or less with respect to the vertical direction.

A liquid is transferred, distributed and mixed in the substrate 10 for sample analysis by using various chambers and channels formed inside the substrate 10 for sample analysis. For example, where a first chamber, a second chamber and a channel connecting between these chambers are provided in the substrate 10 for sample analysis, a liquid injected into the first chamber is transferred into the second chamber via the channel. For example, where a first chamber, a second chamber, a third chamber, a first channel connecting between the first chamber and the second chamber, and a second channel connecting between the first chamber and the third chamber are provided in the substrate 10 for sample analysis, a liquid injected into the first chamber is distributed between the second chamber and the third chamber via the first channel and the second channel. For example, where a first chamber, a second chamber, a third chamber, a first channel connecting between the first chamber and the third chamber, a second channel connecting between the second chamber and the third chamber are provided in the substrate 10 for sample analysis, liquids injected into the first and second chambers are transferred into the third chamber to be mixed together in the third chamber.

Transfer of a liquid between chambers via channels can be achieved by any of various methods. For example, the substrate 10 for sample analysis is supported with the rotation axis P inclined in the range of greater than 0° and 90° or less with respect to the vertical direction. Then, the rotational angle position of the substrate 10 for sample analysis is changed, whereby the chamber from which the liquid is transferred is located higher than the chamber to which the liquid is transferred. Now, "higher" means higher in the vertical direction. Thus, it is possible to transfer a liquid to another chamber by using the gravity. In this case, the channel connecting between chambers is not a capillary channel. The substrate 10 for sample analysis is preferably supported with the rotation axis P inclined by 5° or more with respect to the vertical direction. The rotation axis P of the substrate 10 for sample analysis is more preferably 10° or more and 45° or less with respect to the vertical direction. The substrate 10 for sample analysis is even more preferably supported with the rotation axis P inclined in the range of 20° or more and 30° or less with respect to the vertical direction. This is because if the substrate 10 for sample analysis is supported with an inclination angle less than 5°, the gravity acting upon the liquid in the substrate 10 for sample analysis may be insufficient to provide a driving force needed to transfer the liquid. The term "capillary channel" refers to a channel having a narrow space such that the inside of the capillary channel can be filled with a liquid by virtue of the capillary tube action. A capillary tube is referred to also as a capillary channel. For example, the cross section perpendicular to the direction in which the capillary channel extends may have a width of 0.1 mm to 5 mm and a depth of 50 μm to 300 μm, a width of 50 μm or more (preferably 50 μm to 300 μm) and a depth of 0.1 mm to 5 mm, or a width of 5 mm or less and a depth of 50 μm to 300 μm.

Transfer of a liquid through a capillary channel will now be described by using an example configuration having a first chamber and a second chamber, which are not capillary spaces, and a capillary channel connecting between the first chamber and the second chamber. As a liquid held in the first chamber comes into contact with the opening, which is the connecting portion between the first chamber and the capillary channel, the liquid is sucked into the capillary channel by the capillary force, thereby filling the inside of the channel with the liquid. Now, consider a case where the substrate 10 for sample analysis is rotated at a rotation speed such that the centrifugal force acting upon the liquid inside the capillary channel due to the rotation of the substrate 10 for sample analysis is less than or equal to the capillary force acting upon the liquid inside the capillary channel (including a case where the rotation of the substrate 10 for sample analysis is stopped). In this state, the liquid inside the capillary channel is not transferred into the second chamber but stays in the capillary space. Thus, in order to fill the inside of the capillary channel with a liquid by virtue of the capillary action, an air vent (an air passage between the external environment and the chamber) needs to be provided on the second chamber side, i.e., at the outlet of the capillary channel. Moreover, in order to transfer a liquid by using the capillary action inside a closed space such as the first chamber, the second chamber and the capillary channel, an air vent needs to be provided also on the first chamber side, i.e., at the inlet of the capillary channel, in view of the air pressure in the chambers and in the channel.

Then, with the capillary channel filled with a liquid, the substrate 10 for sample analysis is rotated at a rotation speed such that the centrifugal force acting upon the liquid inside the capillary channel due to the rotation of the substrate 10 for sample analysis is greater than the capillary force acing upon the liquid inside the capillary channel. The liquid inside the first chamber can be transferred into the second chamber if the second chamber is located farther away from the rotation axis P than the first chamber.

Note that the capillary force can be improved by performing a hydrophilic treatment on the wall surface inside the capillary channel. The hydrophilic treatment can be done by applying a non-ionic, cationic, anionic or amphoteric ionic surfactant on the wall surface of the first chamber and each liquid sample spot application port, by performing a corona discharge treatment thereon, by physically forming minute irregularities on the surface, and the like (see, for example, Japanese Laid-Open Patent Publication No. 2007-3361).

The substrate 10 for sample analysis does not need to be disc-shaped. For example, the substrate 10 for sample analysis may be sector-shaped, or may employ any of various shapes such as square, rectangular, diamond-shaped, hexagonal, etc.

The substrate 10 for sample analysis includes a base substrate 12, a magnet 16a, a balancer 16b, a magnet-accommodating chamber 18a and a balancer-accommodating chamber 18b.

The base substrate 12 is a member having a predetermined thickness, with the above-described rotation axis P running therethrough. The base substrate 12 is preferably formed to having a transmittance of 60% or more, using a material such as an acrylic, a polycarbonate or a polystyrene.

The magnet 16a is provided for the B/F separation described above. The magnet 16a may be a magnet that is commonly used in an immunoassay of the competitive assay using magnetic particles, and may be a neodymium magnet or a ferrite magnet. FIG. 1B shows a reaction chamber 14. The reaction chamber 14 is a space where magnetic particles are captured by a magnet at least in the B/F separation.

In the present embodiment, the magnet 16a can be inserted/removed into/from the magnet-accommodating chamber 18a of the base substrate 12. The insertion/removal is done from the upper surface of the substrate 10 for sample analysis.

The magnet 16a is inserted into a position in the vicinity of the wall surface of the reaction chamber 14. This wall surface is a surface perpendicular to the direction in which the centrifugal force is exerted. The centrifugal force is a force exerted in the outward direction as the substrate 10 for sample analysis rotates, and is received by a liquid sample containing magnetic particles. The wall surface of the reaction chamber 14 closer to the magnet 16a supports the liquid sample against the centrifugal force while the substrate 10 for sample analysis is rotating.

The balancer 16b is provided so that the center of gravity of the substrate 10 for sample analysis generally coincides with the rotation axis P. As the magnet 16a is attached to the substrate 10 for sample analysis, the center of gravity of the substrate 10 for sample analysis is moved off the rotation axis P. Therefore, the position of the center of gravity is adjusted by the balancer 16b. Note that there is no particular limitation on the shape and material of the balancer 16b.

The phrase "the center of gravity generally coinciding with" means that the coincidence does not need to be exact. The reason is that the position of the center of gravity of the substrate 10 for sample analysis with no sample therein is different from that of the substrate 10 for sample analysis with a sample therein. Moreover, the position of the center of gravity can also be varied by the transfer of a sample, etc. Therefore, the center of gravity of the substrate 10 for sample analysis, unused, does not need to exactly coincide with the rotation axis P. That is, "generally coinciding" means that the center of gravity is such that a sample analysis device 1, to be described below, can rotate the substrate 10 for sample analysis with various liquids, the magnet 16a and the balancer 16b held therein at least at a predetermined rotation speed.

The balancer 16b can be inserted/removed into/from the balancer-accommodating chamber 18b of the base substrate 12. The insertion/removal is done from the upper surface of the substrate 10 for sample analysis.

If the magnet 16a and the balancer 16b are arranged in symmetry with respect to the rotation axis P, the magnet 16a and the balancer 16b may have the same weight. On the other hand, if the magnet 16a and the balancer 16b are not arranged in symmetry with respect to the rotation axis P, there is a need to adjust the weight of the magnet 16a and that of the balancer 16b depending on the positions thereof. The specific weights can be prescribed when designing the substrate 10 for sample analysis. Note that there may be a plurality of magnets 16a, and there may be a plurality of balancers 16b.

When a user inserts the magnet 16a and the balancer 16b into the magnet-accommodating chamber 18a and the balancer-accommodating chamber 18b, respectively, the user may inadvertently switch them around. In order to prevent this, the shape of the magnet 16a may be different from that of the balancer 16b, or the magnet 16a and the balancer 16b may be distinguished from each other by using colors, marks or characters on at least one of them.

The magnet-accommodating chamber 18a and the balancer-accommodating chamber 18b are spaces for accommodating the magnet 16a and the balancer 16b, respectively. For example, the magnet-accommodating chamber 18a and the balancer-accommodating chamber 18b are depressed portions provided in the base substrate 12 so as to be in conformity with the shape of the magnet 16a and the balancer 16b.

Figure 1C:
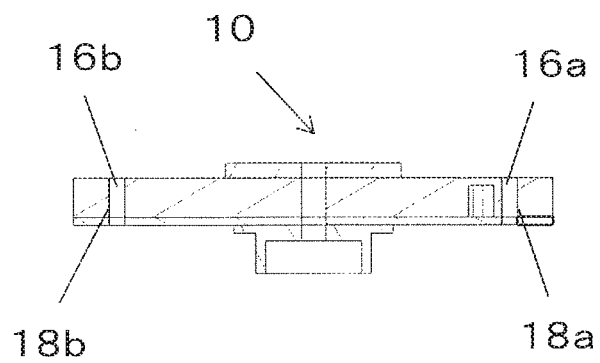
FIG. 1C An example view showing the substrate 10 for sample analysis, with a magnet 16a and a balancer 16b accommodated in a magnet-accommodating chamber 18a and a balancer-accommodating chamber 18b, respectively.

FIG. 1C shows the substrate 10 for sample analysis where the magnet 16a and the balancer 16b are accommodated in the magnet-accommodating chamber 18a and the balancer-accommodating chamber 18b, respectively.

One or both of the magnet 16a and the balancer 16b may be provided fixedly on the base substrate 12. For example, the substrate 10 for sample analysis may be manufactured, used and sold, with the magnet 16a and the balancer 16b both fixed on the base substrate 12. FIG. 1C shows a cross section of the substrate 10 for sample analysis, in the case where the magnet 16a is provided fixedly on the base substrate 12.

Moreover, where the magnet 16a is provided fixedly on the base substrate 12, the position of the magnet 16a may be appropriately changed by design. There is no particular limitation on the position of the magnet 16a on the base substrate 12 as long as magnetic particles can be captured onto one of the wall surfaces inside the reaction chamber 14 (i.e., as long as the magnetic particles can be captured in the chamber). For example, the magnet 16a may be provided on the bottom surface of the reaction chamber 14. Needless to say, an embodiment where the magnet 16a can be inserted/removed may be configured so that the magnet 16a can be inserted into the bottom surface of the reaction chamber 14. For example, the magnet 16a may be provided on the upper surface of the reaction chamber. Needless to say, an embodiment where the magnet 16a can be inserted/removed may be configured so that the magnet 16a can be inserted into the upper surface of the reaction chamber 14.

Figure 2A:
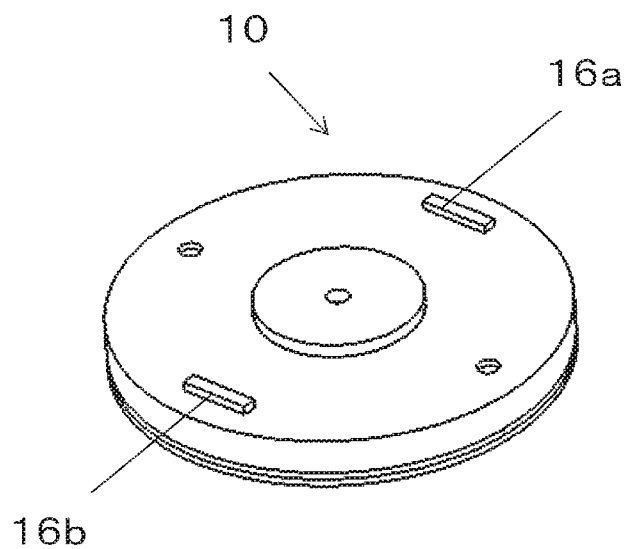
FIG. 2A An example view showing a variation regarding the magnet 16a and the balancer 16b of the substrate 10 for sample analysis.
Figure 2B:
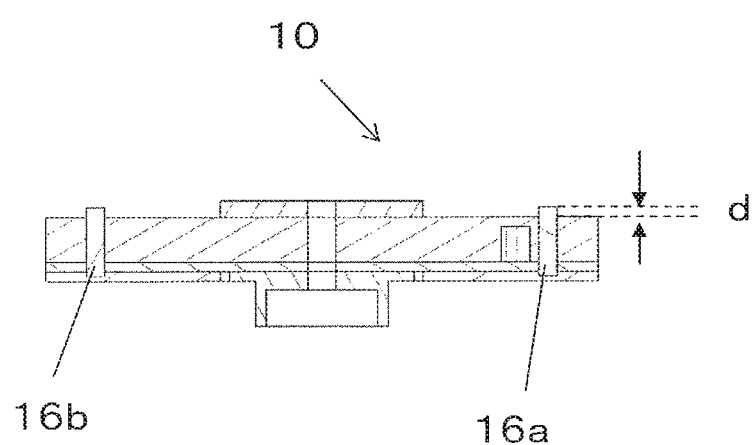
FIG. 2B An example view showing a variation regarding the magnet 16a and the balancer 16b of the substrate 10 for sample analysis.

FIG. 2A and FIG. 2B show a variation regarding the magnet 16a and the balancer 16b of the substrate 10 for sample analysis.

In FIG. 1A to FIG. 1C, the top of the magnet 16a and the top of the balancer 16b are flush with or below the upper surface of the substrate 10 for sample analysis. In the example of FIG. 2A and FIG. 2B, the top of the magnet 16a and the top of the balancer 16b are projecting by a length d from the upper surface of the substrate 10 for sample analysis (see FIG. 2B). This makes it easy to remove the magnet 16a and the balancer 16b. Particularly, it is easier to pull out the magnet 16a and the balancer 16b from the substrate 10 for sample analysis fixed to the sample analysis device before removing the substrate 10 for sample analysis from the sample analysis device.

Figure 3:
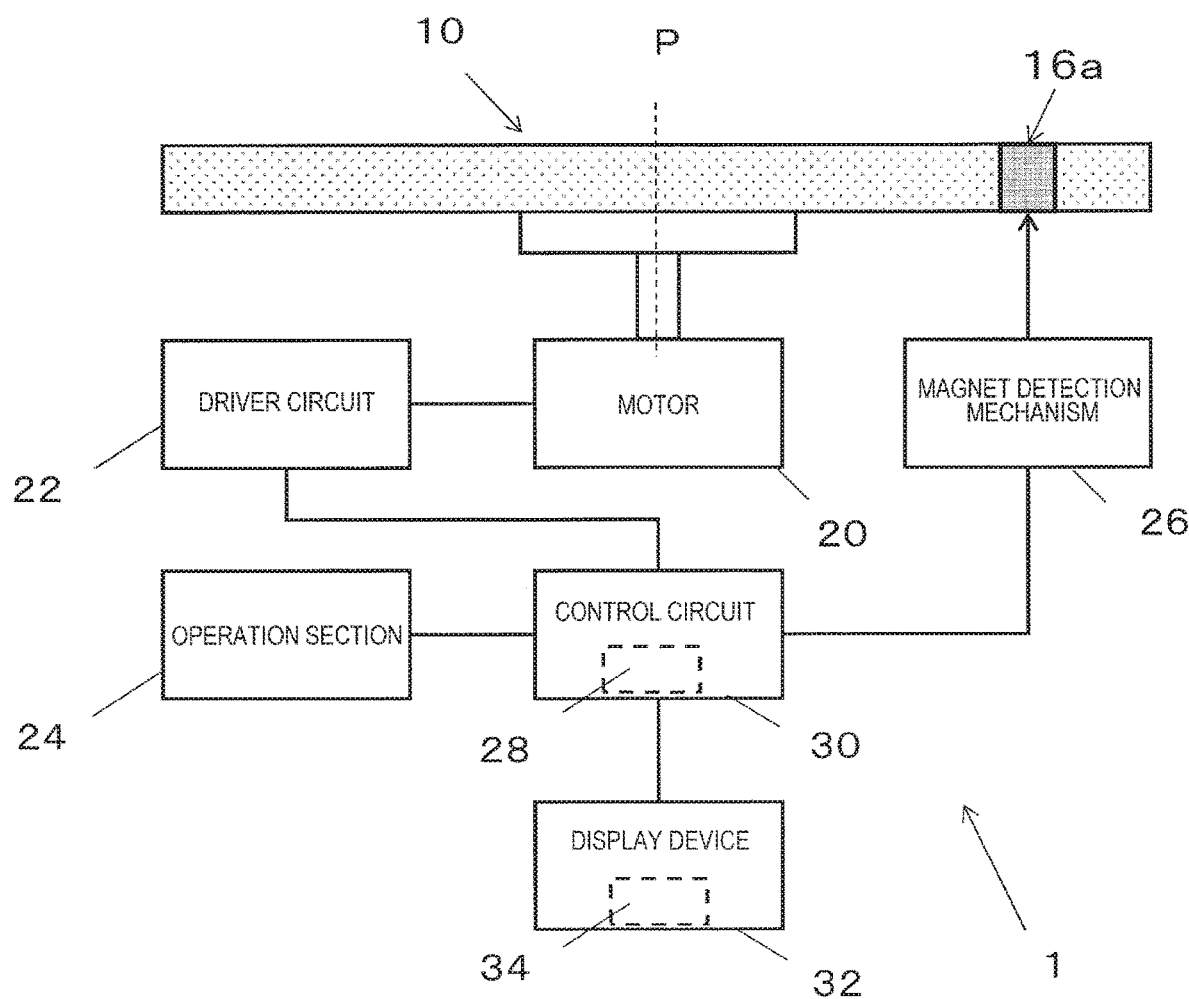
FIG. 3 A diagram showing an example configuration of a sample analysis device 1 according to Embodiment 1.

FIG. 3 shows a configuration of the sample analysis device 1 according to the present embodiment.

The substrate 10 for sample analysis, which has been loaded (set) in the sample analysis device 1, is rotated clockwise or counterclockwise, shaken and stopped at a predetermined position by the sample analysis device 1. Thus, the sample analysis device 1 can transfer, mix and analyze a liquid in the reaction chamber 14 in the substrate 10 for sample analysis.

The sample analysis device 1 includes a motor 20, a driver circuit 22, an operation section 24, a magnet detection mechanism 26, a control circuit 30 and a display device 32. The substrate 10 for sample analysis, on its lower surface, is detachably attached to the sample analysis device 1, and is not a component of the sample analysis device 1. Components of the sample analysis device 1 will now be outlined below.

The motor 20 is a brushless motor including a permanent magnet rotor and a coil, for example. For example, the rotor is 12-pole, and the coil is 3-phase. The brushless motor 20 is provided with a plurality of Hall elements. When the substrate 10 for sample analysis is set in the sample analysis device 1, the rotation axis of the motor 20 coincides with the rotation axis P of the substrate 10 for sample analysis, thereby allowing the motor 20 to rotate the substrate 10 for sample analysis. As described above, the angle at which the substrate 10 for sample analysis is attached to the sample analysis device 1 is adjusted so that the motor 20 rotates the substrate 10 for sample analysis with the rotation axis P inclined by 0° or more and 90° or less with respect to the vertical direction.

Note that the motor 20 may be a brush motor or a stepping motor as long as the movement of the motor 20 is translated into the rotation of the substrate 10 for sample analysis.

The driver circuit 22 primarily includes an inverter circuit and a circuit for controlling the operation of the inverter circuit (both not shown). The driver circuit 22 switches the current flow to the 3 phases of coils of the motor 20 in accordance with the rotation of the rotor of the motor 20, thereby controlling the rotation of the motor 20.

The operation section 24 is an input device such as a touchscreen panel, a keyboard, or the like, and is used by a user for making necessary inputs for operating the sample analysis device 1. The operation section 24 may also be used for starting a magnet detection process to be described below.

The magnet detection mechanism 26 detects whether or not the magnet 16a has been placed in the substrate 10 for sample analysis at the time of measurement. The specific configuration of the magnet detection mechanism 26 varies depending on the detection method. A plurality of configurations will now be described.

The control circuit 30 is a CPU provided in the sample analysis device 1, for example. The control circuit 30 executes a computer program loaded on the RAM (not shown), thereby sending instructions to other circuits in accordance with the procedure of the computer program. Circuits receiving instructions operate as will be described hereinbelow, thereby implementing the functions of the circuits. Instructions from the control circuit 30 are sent to the driver circuit 22, the operation section 24, the magnet detection mechanism 26, the display device 32, etc., as shown in FIG. 3, for example. Procedures of the computer program are illustrated in the flowcharts of the accompanying drawings.

Note that the RAM loaded with a computer program, in other words, the RAM storing a computer program, may be volatile or non-volatile. A volatile RAM is a RAM that cannot retain information stored thereon unless it is receiving power supply. For example, a dynamic random access memory (DRAM) is a typical volatile RAM. A non-volatile RAM is a RAM that can retain information without power supply thereto. For example, a magnetoresistance RAM (MRAM), a resistive RAM (ReRAM) and a ferroelectric memory (FeRAM) are example non-volatile RAMs. In the present embodiment, a non-volatile RAM is preferably employed. A volatile RAM and a non-volatile RAM are both examples of non-transitory computer-readable recording media. A magnetic recording medium such as a hard disk and an optical recording medium such as an optical disc are also examples of non-transitory computer-readable recording media. That is, the computer program of the present disclosure may be recorded on any of various non-transitory computer-readable media, other than media (transitory media) such as the air capable of propagating the computer program as a radio signal.

The display device 32 is a liquid crystal display device, for example, for receiving and displaying a video signal output from the control circuit 30. Assuming that the operation section 24 is a touch panel, the operation section 24 can be provided as a part of the display device 32. In the present specification, the display device 32 is described as being provided in the sample analysis device 1. However, this configuration is merely an example. The display device 32 may be a device external to the sample analysis device 1.

In the present embodiment, the control circuit 30 includes a signal generation circuit 28, and the display device 32 includes a speaker 34.

When the detection result from the magnet detection mechanism 26 indicates an error, i.e., indicates that no magnet is detected, the signal generation circuit 28 generates a signal (notification signal) for outputting a sound, light or an image from the display device 32 or the speaker 34. For example, the sound may be a warning beep, and the light may be warning light. The image may be a message such as "No magnet attached", and displayed on the display device 32.

In the present specification, there is no particular limitation on the embodiment of the notification signal as long as it can be visually or audibly recognized by a user.

The operation of the sample analysis device 1 will now be described with reference to FIG. 4.

Figure 4:
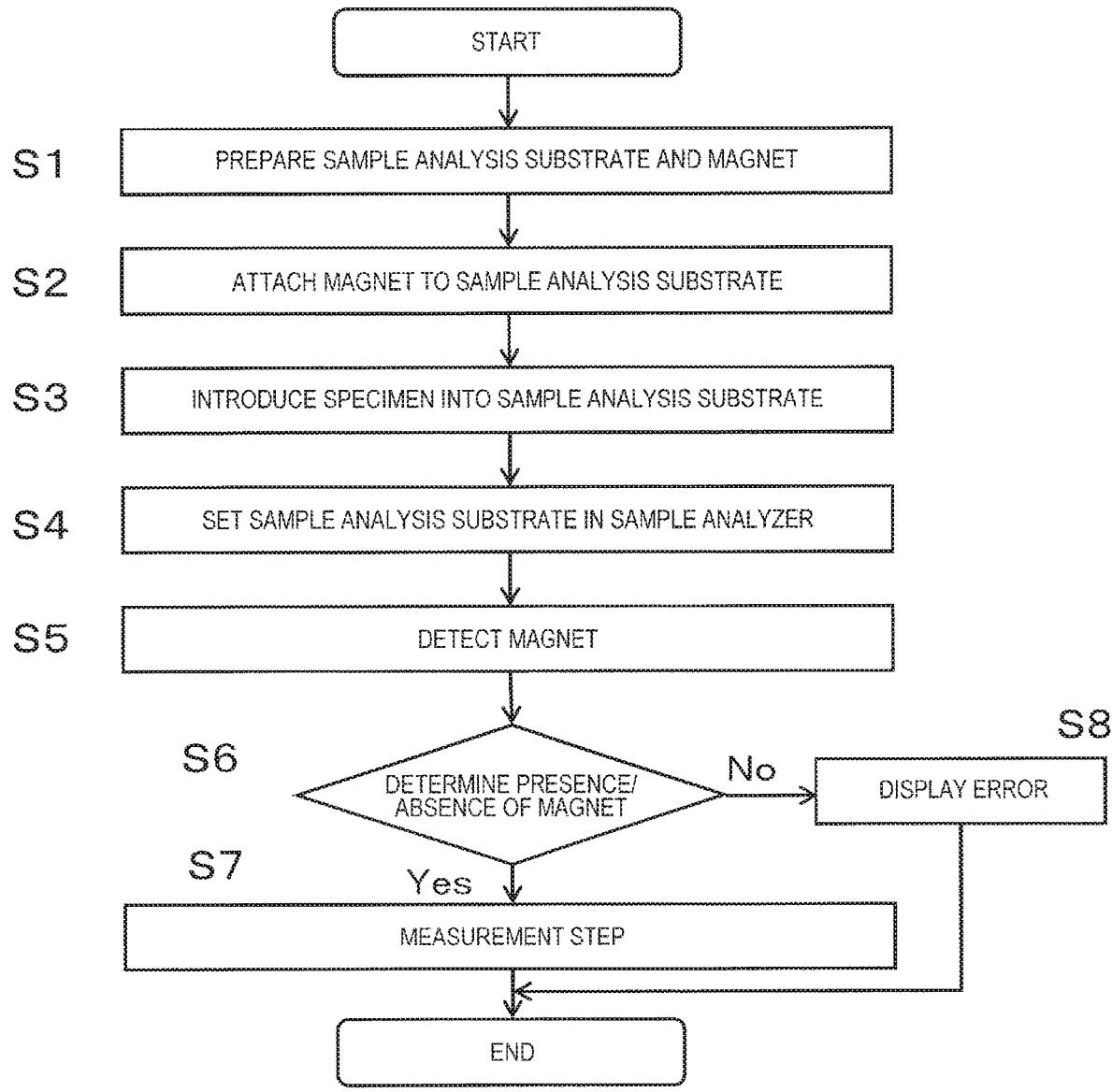
FIG. 4 An example flowchart showing a procedure for measuring a sample using the sample analysis device 1.

FIG. 4 shows an example procedure for measuring a sample using the sample analysis device 1.

Steps S1 to S4 are operations done by a user of the sample analysis device 1, and step S5 and subsequent steps are operations performed by the sample analysis device 1.

The user prepares the substrate 10 for sample analysis and the magnet 16a in step S1. The user attaches the magnet 16a to the substrate 10 for sample analysis in step S2. As necessary, the user may prepare the balancer 16b in step S1, and attach the balancer 16b in step S2. Upon attachment, there is obtained the substrate 10 for sample analysis as shown in FIG. 1C or FIG. 2A and FIG. 2B.

The user introduces a sample (analyte) in the substrate 10 for sample analysis in step S3, and sets the substrate 10 for sample analysis in the sample analysis device 1 in step S4. Through this operation, the substrate 10 for sample analysis is rotatably fixed on the sample analysis device 1.

In step S5, the control circuit 30 causes the magnet detection mechanism 26 to execute a detection process for detecting the magnet 16a.

In step S6, the magnet detection mechanism 26 determines the presence/absence of the magnet 16a. The details of the determination process will be described below. As a result of the determination, control proceeds to step S7 if the magnet 16a is present, and proceeds to step S8 if the magnet 16a is absent.

In step S7, the control circuit 30 performs operations including shaking, rotating and stopping the substrate 10 for sample analysis in accordance with a predetermined procedure to measure the sample. The description of the specific details of the measurement is omitted in the present specification.

In step S8, if the control circuit 30 receives a signal indicating that the detection result from the magnet detection mechanism 26 is an error, the signal generation circuit 28 generates a notification signal. The display device 32 displays the error based on the notification signal.

A specific example of the magnet detection mechanism 26 will now be described. Detection methods used by the magnet detection mechanism 26 herein include those using the optical characteristic or the magnetic characteristic of the substrate 10 for sample analysis, the weight thereof, the current or voltage value depending on the rotational load, the rotational acceleration, and the steady rotation speed. Note that these detection methods do not need to be employed alternatively. The magnet detection mechanism 26 detects the magnet 16a by using at least one method.

Note that while descriptions will now be made using block diagrams as necessary, only components related to the magnet detection will be described, and other components will not be described.

Figure 5:
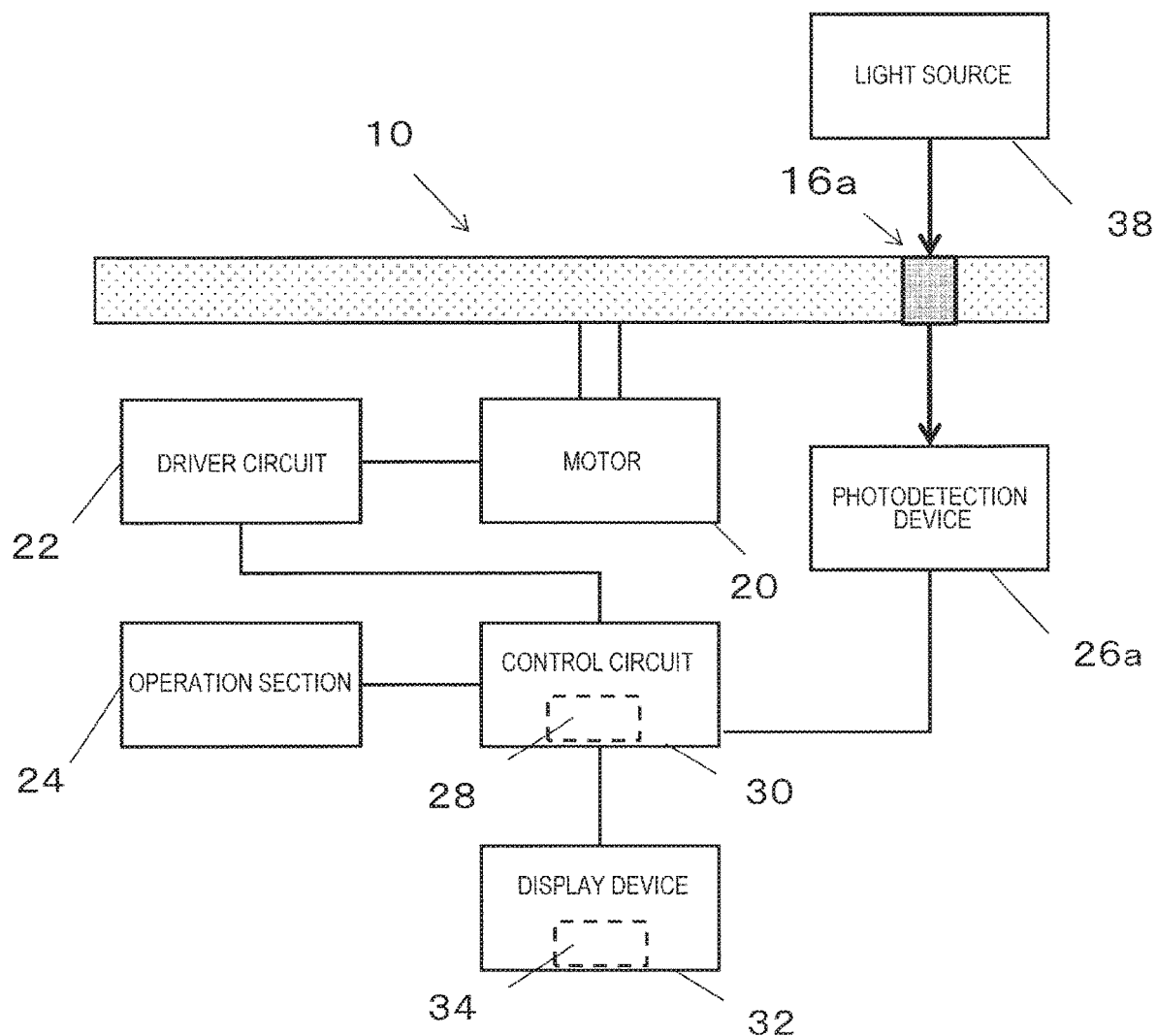

FIG. 5 shows an example configuration of the sample analysis device 1 for optically detecting the magnet 16a. A photodetection device 26a and a light source 38 are provided as the magnet detection mechanism 26.

The photodetection device 26a includes a light receiving element (not shown), a driver circuit and a voltage conversion circuit. In the photodetection device 26a, the light receiving element generates a current value signal through photoelectric conversion under the control of the driver circuit, and the current value signal is converted into a voltage value signal. The voltage conversion circuit outputs the voltage value signal to the control circuit 30, and the control circuit 30 determines the presence/absence of the magnet by using the signal. Note that the photodetection device 26a may be provided with an arithmetic circuit so that the photodetection device 26a determines the presence/absence of the magnet 16a. The light receiving element is arranged at a position such that it can receive light output from the light source 38. The light source 38 is arranged at a position such that the magnet in the substrate 10 for sample analysis can be illuminated when the substrate 10 for sample analysis is attached to the sample analysis device 1 and the substrate 10 for sample analysis is rotated.

Figure 6:
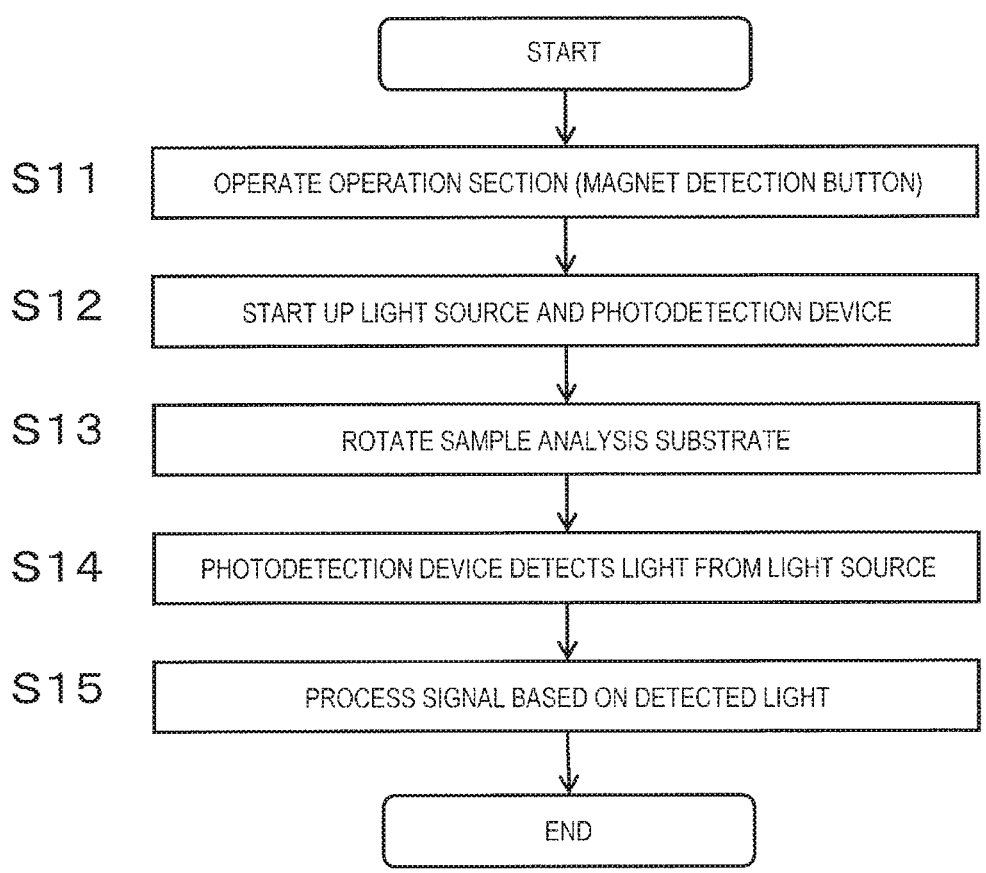
FIG. 6 An example flowchart showing a procedure of a method for detecting the magnet 16a by using an optical characteristic.

FIG. 6 shows a procedure of a method for detecting the magnet 16a by using the optical characteristic.

In step S11, the user operates the operation section 24 to instruct to start the magnet detection. For example, where a magnet detection start button is provided as hardware, step S11 corresponds to the process of accepting a press-down of the button.

In step S12, the control circuit 30 starts up the photodetection device 26a and the light source 38.

In step S13, the motor 20 rotates the substrate 10 for sample analysis.

In step S14, the photodetection device 26a starts detecting light from the light source 38.

In step S15, the control circuit 30 processes signals based on light detected by the photodetection device 26a to determine the presence/absence of the magnet 16a. The details of this process will now be described with reference to FIG. 7.

Figure 7:
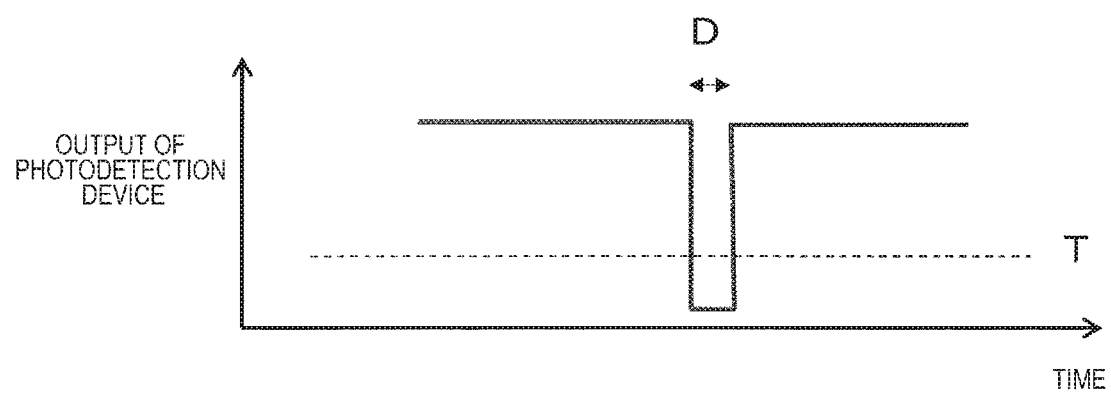

FIG. 7 shows an output result of the photodetection device 26a. This example shows an output result obtained for one rotation of the substrate 10 for sample analysis, assuming that the magnet 16a is attached. The horizontal axis represents time, and the vertical axis represents the detection result (output) of the photodetection device 26a.

When the rotation starts, light from the light source 38 is detected by the photodetection device 26a since the base substrate 12 allows light to pass therethrough. As the rotation continues, light hits the magnet 16a. Since the magnet 16a has zero transmittance, the photodetection device 26a does not detect light while the magnet 16a is passing therethrough. In FIG. 7, the period D corresponds to the period over which the magnet 16a is passing therethrough. Then, after the magnet 16a has passed therethrough, the photodetection device 26a again detects light from the light source 38.

As can be seen from the detection waveform of FIG. 7, the control circuit 30 sets a threshold value T, and the control circuit 30 can determine that the magnet 16a is attached if there is the period D over which the output is below the value. On the other hand, if the magnet is not attached, there will be no period over which the output is below the threshold value T. In such a case, the control circuit 30 can determine that the magnet 16a is not attached.

Note that if the balancer 16b is formed by a material having a low transmittance, it is preferred that the magnet 16a and the balancer 16b are located at radially different positions. This is to prevent an erroneous detection when the balancer 16b is attached and the magnet 16a is not attached.

Note that even if the substrate 10 for sample analysis is configured so that the magnet 16a and the balancer 16b are provided at the same radial positions, they can be distinguished from each other based on their shapes. Specifically, the magnet 16a and the balancer 16b may be made different from each other in terms of their lengths in the rotation direction. For one rotation of the substrate 10 for sample analysis, with the magnet 16a and the balancer 16b attached, there will be two periods in which the output result is below the threshold value T. If the magnet 16a and the balancer 16b different from each other in terms of their lengths in the rotation direction, the period over which the output is below threshold value T will differ therebetween. Therefore, if the magnet 16a and the balancer 16b are shaped so that they have different lengths in the rotation direction, it is possible to determine the presence/absence of each of the magnet 16a and the balancer 16b.

If the transmittance of the balancer 16b for light from the light source 38 is made different from that of the magnet 16a, it is possible to distinguish the magnet 16a and the balancer 16b from each other. For example, the transmittance for light from the light source 38 can be set as follows by changing the material, etc.

Transmittance of magnet 16a<Transmittance of balancer 16b<Transmittance of base substrate 12

For example, with two threshold values (T1 and T2; T1<T2) set in advance, one may determined that the magnet 16a is present in the substrate 10 for sample analysis if there is a period over which the output result is lower than the threshold value T1, and that the balancer 16b is present if there is a period over which the output result is lower than the threshold value T2 and higher than the threshold value T1. Also with such a configuration, it is possible to determine the presence/absence of each of the magnet 16a and the balancer 16b.

Figure 8:
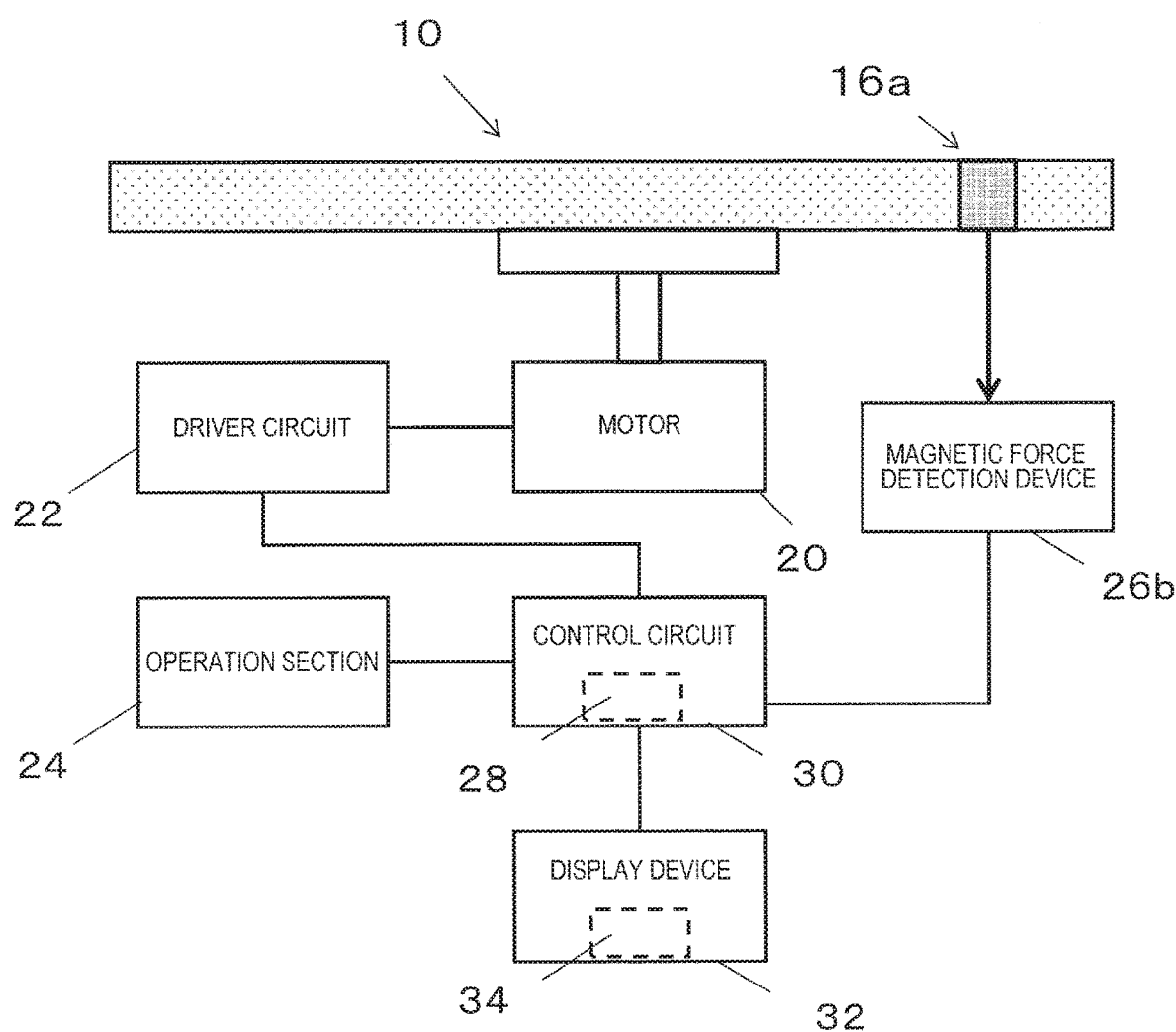

FIG. 8 shows an example configuration of the sample analysis device 1 for detecting the presence/absence of a magnetic force of the magnet 16a. The magnetic force detection device 26b is provided as the magnet detection mechanism 26.

The magnetic force detection device 26b includes, for example, an element for outputting a voltage or opening/closing a switch in accordance with the magnetic force, a driver circuit and a voltage conversion circuit. The element for outputting a voltage in accordance with the magnetic force may be a Hall element. The element for opening/closing a switch in accordance with the magnetic force may be a reed switch. An example using a Hall element will now be described.

The magnetic force detection device 26b outputs the voltage signal from a Hall element to the control circuit 30, and the control circuit 30 determines the presence/absence of the magnet. Note that the magnetic force detection device 26b may be provided with an arithmetic circuit, and the photodetection device 26a may determine the presence/absence of the magnet 16a.

Figure 9:
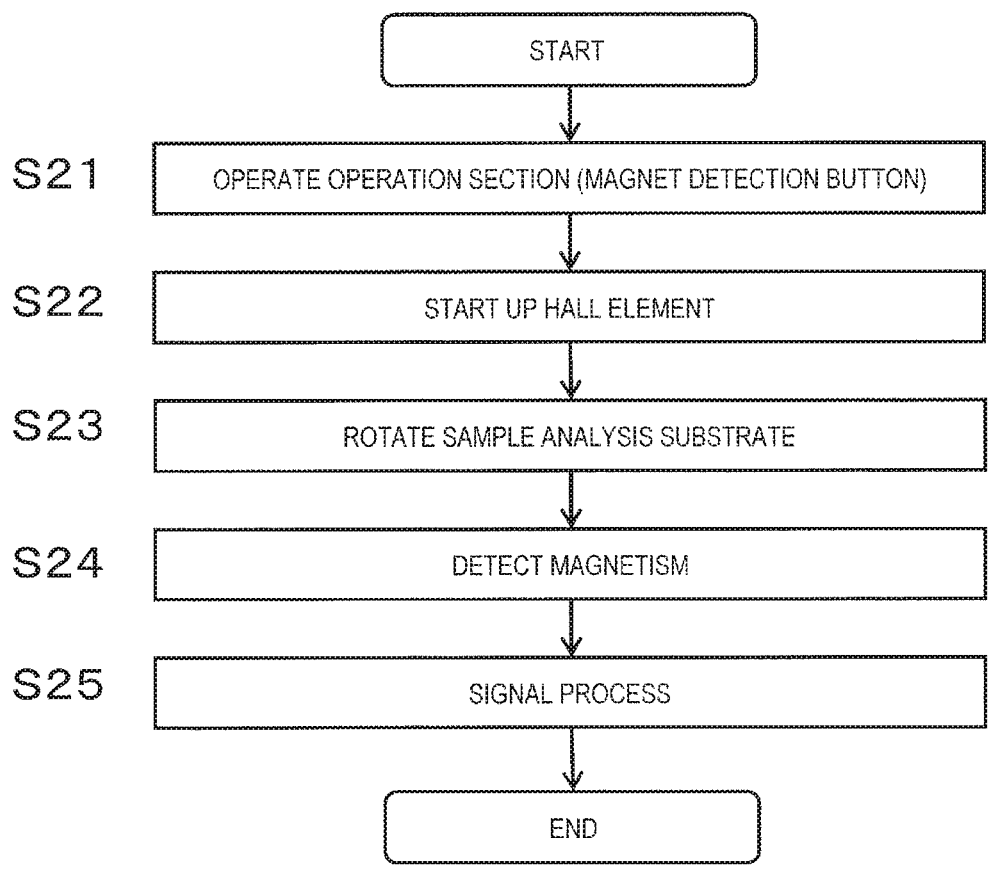
FIG. 9 An example flowchart showing a procedure of a method for detecting the magnet 16a by using a magnetic characteristic.

FIG. 9 shows a procedure of a method for detecting the magnet 16a by using a magnetic characteristic.

In step S21, the user operates the operation section 24 to instruct to start the magnet detection. For example, where a magnet detection start button is provided as hardware, step S21 corresponds to the process of accepting a press-down of the button.

In step S22, the control circuit 30 starts up a Hall element of the magnetic force detection device 26b.

In step S23, the motor 20 rotates the substrate 10 for sample analysis.

In step S24, the Hall element of the magnetic force detection device 26b detects magnetism. The Hall element outputs a voltage signal in accordance with the intensity of the magnetic force.

In step S25, the control circuit 30 processes the voltage signal output from the Hall element of the magnetic force detection device 26b to determine the presence/absence of the magnet 16a. The details of this process will now be described with reference to FIG. 10.

Figure 10:
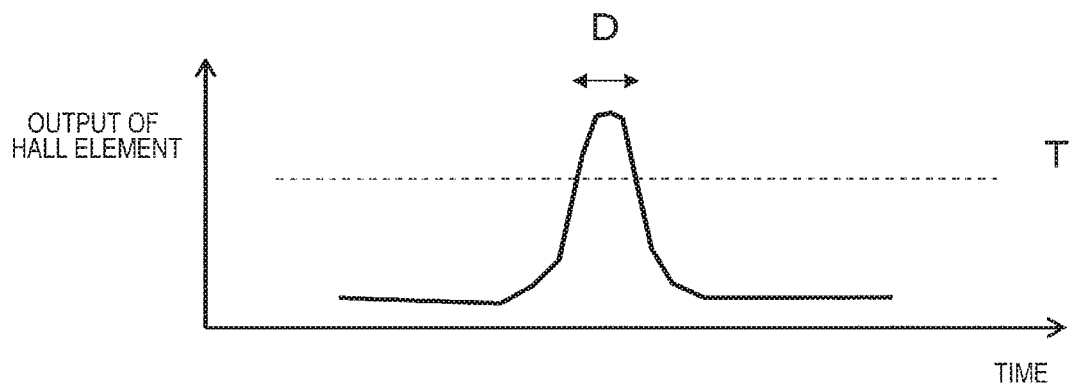
FIG. 10 An example graph showing an output result of a Hall element of a magnetic force detection device 26b.

FIG. 10 shows an output result of the Hall element of the magnetic force detection device 26b. This example shows an output result obtained for one rotation of the substrate 10 for sample analysis, assuming that the magnet 16a is attached. The horizontal axis represents time, and the vertical axis represents the detection result (output) of the magnetic force detection device 26b. Note that FIG. 10 shows the output result under the following conditions.

The magnet 16a is arranged so that the south pole and the north pole are on the lower surface side and the upper surface side, respectively, of the substrate 10 for sample analysis.

The magnetic force detection device 26b detects the magnetic force of the magnet 16a from the lower surface of the substrate 10 for sample analysis.

The Hall element of the magnetic force detection device 26b is configured so that the output voltage becomes positive when the south pole of the magnet 16a comes close.

When the rotation starts, the Hall element outputs only a relatively small voltage in a situation where the magnet 16a and the Hall element are located away from each other. As the rotation continues, the magnet 16a comes closer to the Hall element and then moves away from the Hall element after reaching the closest point. In FIG. 10, the period D corresponds to a situation where the magnet 16a comes closer to the Hall element and then moves away therefrom after reaching the closest point. After the magnet 16a passes, the magnet 16a and the Hall element move are away from each other, and the Hall element therefore outputs only a relatively small voltage.

As can be seen from the detection waveform of FIG. 10, with a threshold value T set, the control circuit 30 can determine that the magnet 16a is attached if there is the period D over which the output exceeds the value. On the other hand, if the magnet is not attached, there will be no period over which the output exceeds the threshold value T. In such a case, the control circuit 30 can determine that the magnet 16a is not attached.

Note that if the detection sensitivity of the Hall element of the magnetic force detection device 26b is sufficiently high and/or the magnetic force of the magnet 16a is sufficiently strong, it is possible to detect the magnet only by setting the sample analysis device 1 in the substrate 10 for sample analysis without the motor 20 rotating the substrate 10 for sample analysis. In such a case, the process of step S23 is not needed. The control circuit 30 may determine that the magnet 16a is attached if the output of the Hall element exceeds a predetermined threshold value and that the magnet 16a is not attached if the output does not exceed the predetermined threshold value.

Figure 11:
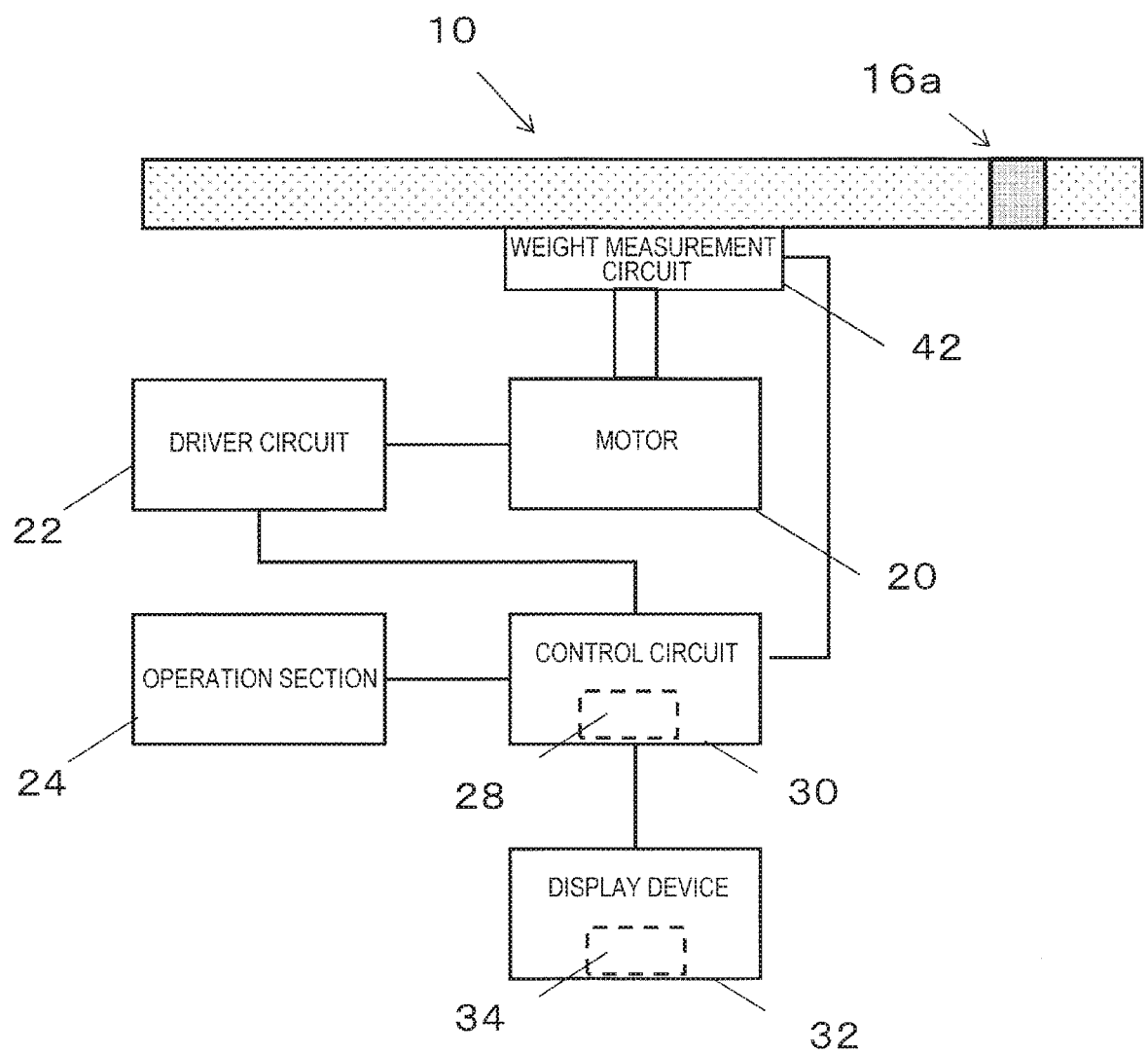
FIG. 11 An example diagram showing an example configuration of the sample analysis device 1 for detecting the presence/absence of the magnet 16a based on the weight of the substrate 10 for sample analysis.

FIG. 11 shows an example configuration of the sample analysis device 1 for detecting the presence/absence of the magnet 16a based on the weight of the substrate 10 for sample analysis. A weight measurement circuit 42 is provided as the magnet detection mechanism 26. Note that as will be discussed below, the operation is relatively simple, and a description using a flowchart will be omitted. Note however that as long as the control circuit 30 operates, the process thereof can be implemented by a program to be executed as follows.

The weight measurement circuit 42 is a strain gauge, which is a mechanical sensor for measuring the strain of an object, for example. The load to be sensed by the strain gauge and the amount of strain will be specified in advance at the time of design, depending on the type of a strain gauge to be used.

For example, assume that the weight of the substrate for sample analysis is 14.0 grams and the magnet 16a by itself weighs 0.7 gram. The control circuit 30 can detect the current load based on the amount of strain of the weight measurement circuit 42. If it is indicated that the load is 14.7 grams, the control circuit 30 can determine that the magnet 16a is present in the substrate 10 for sample analysis. On the other hand, if it is indicated that the load is 14.0 grams, the control circuit 30 can determine that the magnet 16a is absent in the substrate 10 for sample analysis.

Figure 12:
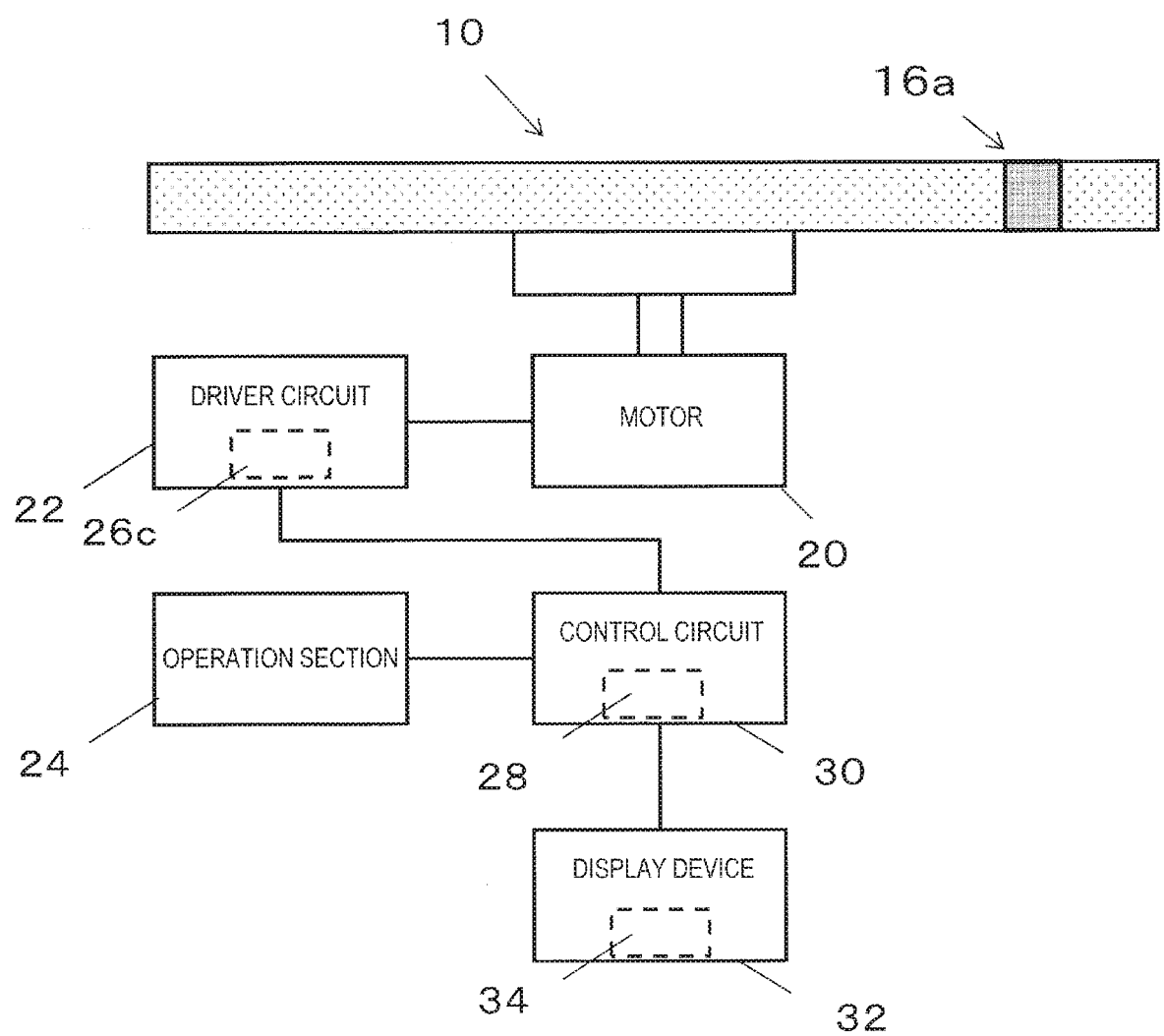
FIG. 12 An example diagram showing an example configuration of the sample analysis device 1 for detecting the presence/absence of the magnet 16a based on the motor rotational load when the substrate 10 for sample analysis is set.

FIG. 12 shows an example configuration of the sample analysis device 1 for detecting the presence/absence of the magnet 16a based on the motor rotational load when the substrate 10 for sample analysis is set. A load detection circuit 26c is provided in the driver circuit 22 as the magnet detection mechanism 26. Note that as will be discussed below, the operation is relatively simple, and a description using a flowchart will be omitted. Note however that as long as the control circuit 30 operates, the process thereof can be implemented by a program to be executed as follows.

The load detection circuit 26c detects the rotational load of the motor 20. The rotational load varies dependent on the weight of the substrate 10 for sample analysis to be rotated. The operating principle of this example utilizes the fact that the weight of the magnet 16a increases the load on the motor 20 rotating the substrate 10 for sample analysis. That is, it is possible to determine whether or not the magnet 16a is present based on the load on the motor 20 detected by the load detection circuit 26c.

Specifically, the motor 20 driven by the driver circuit 22 rotates the substrate 10 for sample analysis at a constant rotation speed (e.g., 1000 rpm), and the load detection circuit 26c measures the value of the load current. The value X1 of the load current to be measured when the magnet 16a is present and the value X2 of the load current to be measured when the magnet 16a is absent are specified in advance at the time of design. When the magnet 16a is present, the load increases by the weight of the magnet 16a. Therefore, the values X1 and X2 have the relationship of X1>X2. The control circuit 30 can determine the presence/absence of the magnet 16a based on the value of the load current measured by the load detection circuit 26c.

Note that a constant load current may be provided to the motor 20 to rotate the substrate 10 for sample analysis, and then the rotation speed can be measured to determine the presence/absence of the magnet 16a.

Specifically, the motor 20 driven by the driver circuit 22 rotates the substrate 10 for sample analysis at a constant rotation speed (e.g., 1000 rpm), and then the load detection circuit 26c measures the rotation speed. The value X3 of the rotation speed to be measured when the magnet 16a is present and the value X4 of the rotation speed to be measured when the magnet 16a is absent are specified in advance at the time of design. When the magnet 16a is present, the load increases by the weight of the magnet 16a. Therefore, the values X3 and X4 have the relationship of X3<X4. The control circuit 30 can determine the presence/absence of the magnet 16a based on the value of the rotation speed measured by the load detection circuit 26c.

Note that there may be a case where only one of the magnet 16a and the balancer 16b is placed in the substrate 10 for sample analysis. Such a substrate 10 for sample analysis is not well-balanced, and the actual rotation speed will be lower than the expected rotation speed. Thus, the presence/absence of the magnet 16a can be detected based on the rotation speed (steady rotation speed) at the point in time when the rotation becomes stable eventually. The control circuit 30 may use a notification signal to notify the user of the presence/absence of the magnet 16a, or the absence of one of the magnet 16a and the balancer 16b.

When the load current value is measured as the unbalanced substrate 10 for sample analysis is rotated by the motor 20, the actual current value will be different from the expected current value. Therefore, based on this current value, the control circuit 30 can use a notification signal to notify the user of the absence of the magnet 16a or the balancer 16b.

Although the load current value is measured in the example described above, the driving voltage may be measured. The acceleration value used when increasing the rotation speed varies depending on the presence/absence of the magnet 16a (including the balancer 16b). The acceleration of the substrate 10 for sample analysis in which the magnet 16a is present is smaller than the acceleration of the substrate 10 for sample analysis in which the magnet 16a is absent. Any of the acceleration values can be specified by design. The presence/absence of the magnet 16a can be detected by using such acceleration. Various methods are possible for detecting the acceleration. For example, where a Hall element is provided in the motor 20, the driver circuit 22 can determine the acceleration of the rotor of the motor 20, i.e., the value of the rotational acceleration of the substrate 10 for sample analysis, based on the output value of the Hall element.

Next, a variation of the substrate 10 for sample analysis will be described with reference to FIG. 13A to FIG. 13C, FIG. 14A, FIG. 14B, FIG. 15A and FIG. 15B.

Figure 13A:
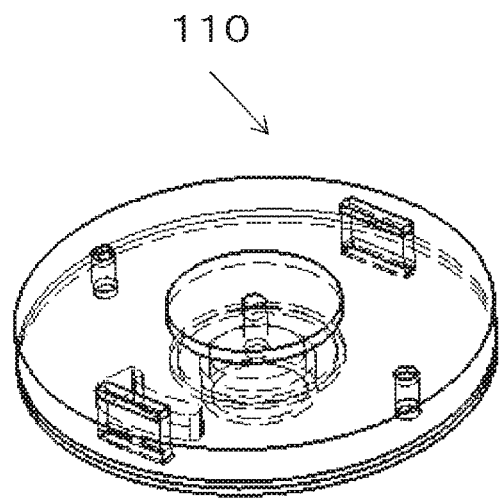
FIG. 13A An example view showing the external appearance of a substrate 110 for sample analysis according to a variation.

FIG. 13A shows the external appearance of a substrate 110 for sample analysis according to the variation. The substrate 10 for sample analysis described above is configured so that the magnet 16a, the balancer 16b, and the like, can be removed, as parts, from the base substrate 12.

The substrate 110 for sample analysis is includes two parts combined together.

Figure 13B:
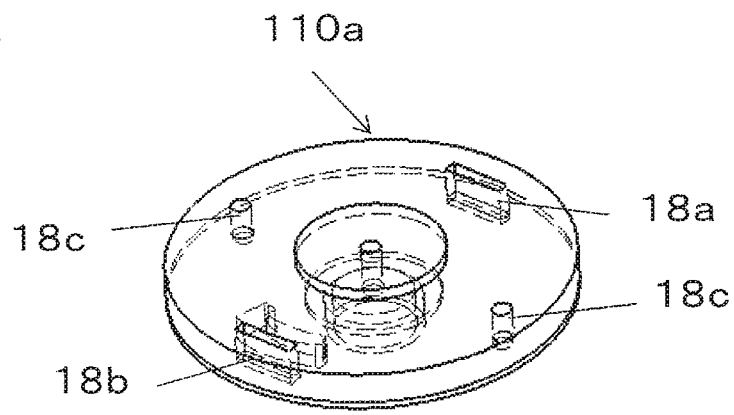
FIG. 13B An example view showing a base substrate 110a of the substrate 110 for sample analysis.
Figure 13C:
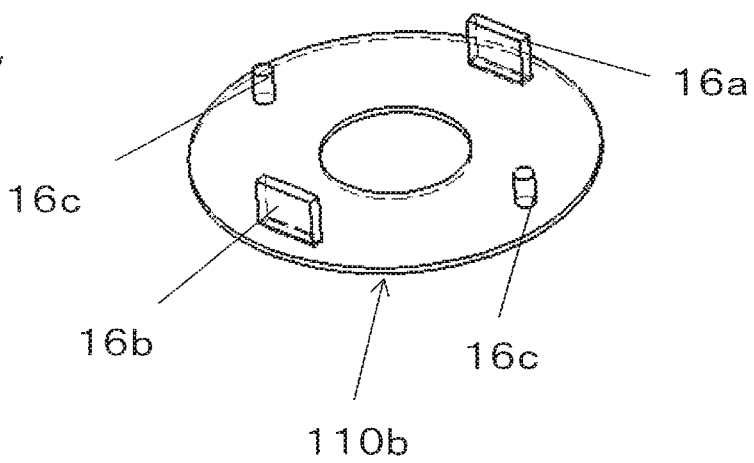
FIG. 13C An example view showing a magnet unit 110b of the substrate 110 for sample analysis.

FIG. 13B shows a base substrate 110a of the substrate 110 for sample analysis, and FIG. 13C shows a magnet unit 110b of the substrate 110 for sample analysis. The substrate 110 for sample analysis includes the base substrate 110a and the magnet unit 110b to be fitted together.

As shown in FIG. 13B, the base substrate 110a includes the magnet-accommodating chamber 18a and the balancer-accommodating chamber 18b. Moreover, the base substrate 110a includes a plurality of fixation holes 18c. Note that there is no particular limitation on the number of holes 18c.

On the other hand, as shown in FIG. 13C, the magnet unit 110b is provided with the magnet 16a and the balancer 16b, and is further provided with fixation bosses 16c. In this variation, the magnet 16a and the balancer 16b are fixed to the magnet unit 110b.

Figure 14A:
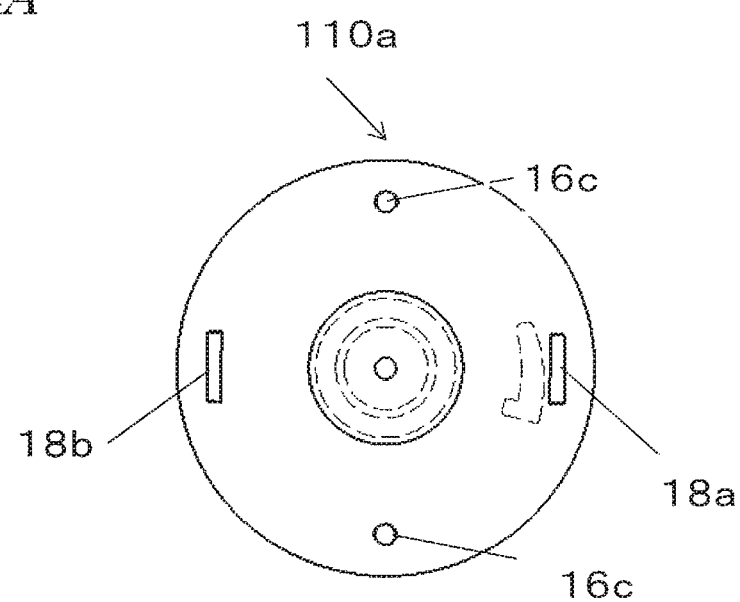
Figure 14B:
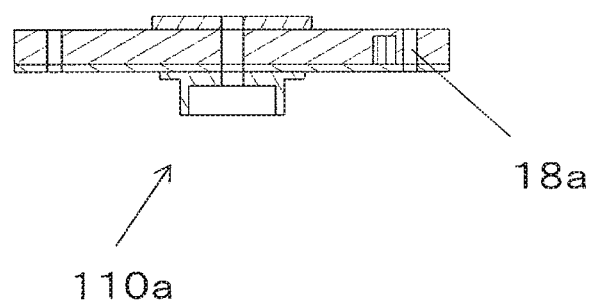

FIG. 14A and FIG. 14B are a top view and a cross-sectional view of the base substrate 110a.

Figure 15A:
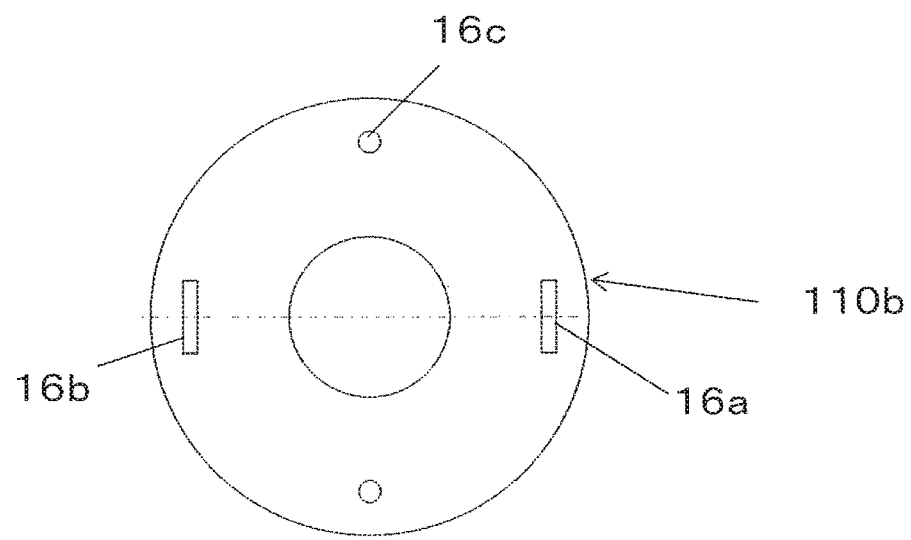
FIG. 15A An example top view showing the magnet unit 110b.
Figure 15B:
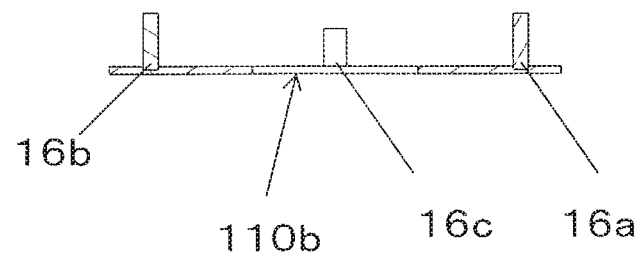
FIG. 15B An example side view showing the magnet unit 110b.

FIG. 15A and FIG. 15B are a top view and a side view of the magnet unit 110b.

The magnet 16a and the balancer 16b are inserted into the magnet-accommodating chamber 18a and the balancer-accommodating chamber 18b, and the fixation bosses 16c are inserted into the fixation holes 18c, thereby fixing the substrate 110 for sample analysis with respect to the rotation direction.

Note that although the magnet unit 110b is provided to be attached to the base substrate 110a at the lower surface so as to be detachable off the lower surface in the example of FIGS. 13A to 15B, this is merely an example. For example, the magnet unit 110b may be attached to the base substrate 110a at the upper surface so as to be detachable off the upper surface.

Moreover, the magnet unit 110b may be attached to the base substrate 110a at the side surface so as to be detachable off the side surface. For example, the magnet unit 110b and the base substrate 110a may be configured as if they were pieces of the substrate 10 for sample analysis cut along a plane parallel to the rotation axis. Then, for the sake of discussion, one of the pieces that includes the magnet 16a is referred to as the magnet unit 110b, whereas the other piece including the magnet-accommodating chamber 18a is referred to as the base substrate 110a. With such an illustrative configuration, the magnet unit 110b can be attached to the base substrate 110a at the side surface so as to be detachable off the side surface.

Embodiment 2

Figure 16:
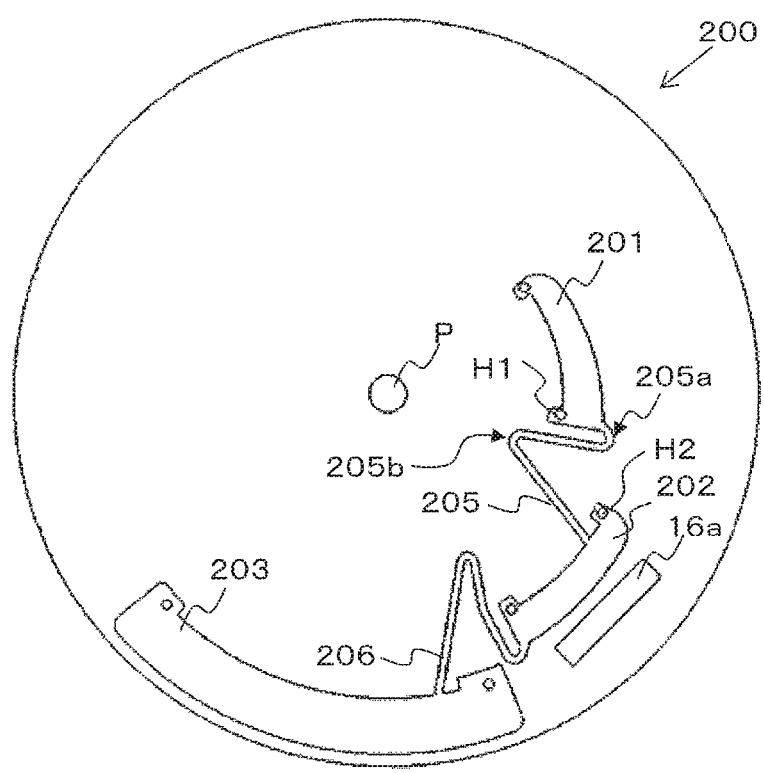
FIG. 16 An example top view (bottom view) showing a substrate 200 for sample analysis.

FIG. 16 is an example top view (or bottom view) of a substrate 200 for sample analysis according to the present embodiment. Note that the definitions of the "upper surface" and the "lower surface" are as set forth above in Embodiment 1 in conjunction with FIG. 1A.

The substrate 200 for sample analysis includes the rotation axis P, the magnet 16a, a first chamber 201 having the first space, a second chamber 202 having the second space, and a third chamber 203 having the third space. Note that FIG. 16 does not show the balancer 16b.

The substrate 200 for sample analysis includes a first channel 205 connecting between the first chamber 201 and the second chamber 202, and a second channel 206 connecting between the second chamber 202 and the third chamber 203. The word "connect" as used herein means to connect chambers together so that a liquid sample can be transferred therebetween.

The shapes of the first chamber 201, the second chamber 202 and the third chamber 203, and the arrangement thereof in the substrate 200 for sample analysis will be described.

First, the first chamber 201 will be described. In the present embodiment, there is no particular limitation on the shape of the first chamber 201. It is basically preferred that the connecting portion between the first chamber 201 and the first channel 205 is located on one of the wall surfaces of the first chamber 201 extending in parallel to the rotation axis that is farthest from the rotation axis (the outermost wall surface) or on a side surface that is adjacent to the outermost wall surface. This is because when transferring a liquid from the first chamber 201 to the second chamber 202, it is possible to prevent some of the liquid from remaining in the first chamber 201. However, it should be noted that this configuration may depend on the shape of the first chamber 201.

Since the first channel 205 is a capillary channel as will be described below, the first chamber 201 needs to have an air vent. FIG. 16 shows example air vents H1 provided in the first chamber 201. Symbols "○" of the same shape in FIG. 16 each denote an air vent. There is no particular limitation the position of each air vent as long as the air vent is not filled with a liquid when a liquid is introduced into the chamber. The position may be on a side surface portion that is close to the rotation axis or on a side surface portion of the side wall that is on the side closer to the rotation axis. This similarly applies to the symbols "○" in the second chamber 202 and the third chamber 203 to be described next.

Next, the second chamber 202 will be described. In the present embodiment, there is no particular limitation on the shape of the second chamber 202. It is basically preferred that the connecting portion between the second chamber 202 and the first channel 205 is located on one of the wall surfaces of the second chamber 202 extending in parallel to the rotation axis that is closest to the rotation axis (the innermost wall surface) or on a side wall that is adjacent to the innermost wall surface (preferably, an inner side portion thereof). However, it should be noted that this configuration may depend on the shape of the second chamber 202.

Where the first channel 205 and the second channel 206 are capillary channels, they need to have (at least one) air vent. FIG. 16 shows example air vents H2 provided in the second chamber 202.

The position of the second chamber 202 needs to be farther away from the rotation axis P than the first chamber 201.

Lastly, the third chamber 203 will be described. The configuration of the third chamber 203 is basically similar to that of the second chamber 202. That is, there is no particular limitation on the shape of the third chamber 203, and the third chamber 203 needs to have an air vent. It is basically preferred that the connecting portion between the third chamber 203 and the second channel 206 is located on one of the wall surfaces of the third chamber 203 extending in parallel to the rotation axis that is closest to the rotation axis (the innermost wall surface) or on a side wall that is adjacent to the innermost wall surface (preferably, an inner side portion thereof). Note however that the position of the third chamber 203 needs to be farther away from the rotation axis P than the second chamber 202.

Next, the first channel 205 and the second channel 206 will be described.

The first channel 205 has a first bend 205a and a second bend 205b along the first channel 205 from the first chamber 201 to the second chamber 202. The first bend 205a has a shape that is projecting away from the rotation axis P, and the second bend 205b has a shape that is projecting toward the rotation axis P. The first bend 205a is located between the first chamber 201 (one of the two chambers 201 and 202 connected together by the first channel 205 that is located closer to the rotation axis P) and the second bend 205b. It is preferred that R1>R2 is satisfied, where R1 is the distance between the rotation axis P and a side surface of the chamber 202 (one of the two chambers 201 and 202 connected together by the first channel 205 that is located farther away from the rotation axis P) that is closest to the rotation axis, and R2 is the distance between the rotation axis P and a point in the first bend 205a that is farthest away from the rotation axis P. It is also preferred that R4>R3 is satisfied, where R4 is the distance from the rotation axis P to the liquid surface of the liquid held in the chamber 201 (located closer to the rotation axis P), where the liquid is held against a side surface of the chamber 201 due to the centrifugal force, and R3 is the distance from the rotation axis P to a point in the second bend 205b that is closest to the rotation axis P.

When the motor 20 is rotating the substrate 200 for sample analysis at a certain rotation speed, a liquid sample is transferred from the first chamber 201 to the second chamber 202 via the first channel 205. While this rotation is maintained, the liquid sample will not be transferred from the second chamber 202 to the third chamber 203. Assuming that the same capillary force acts upon a liquid in the first channel 205 and a liquid in the second channel 206, the "rotation speed" as used herein is such that the centrifugal force acting upon the liquid due to the rotation of the substrate 10 for sample analysis is greater than the capillary force acting upon the liquid in the second channel 206. As the motor 20 rotates the substrate 10 for sample analysis at this rotation speed, thereby transferring the liquid sample from the first chamber 201 to the second chamber 202 via the first channel 205, a part of the liquid sample in the second chamber fills a portion of the second channel 206. That is, although the liquid sample having been transferred to the second chamber 202 is drawn into the second channel 206 due to the capillary force of the second channel 206, the centrifugal force due to the rotation of the substrate 10 for sample analysis is greater than this capillary force. Therefore, the second channel 206 is filled with the liquid sample only to the same height as the height (the distance from the rotation axis P) of the liquid surface of liquid sample in the second chamber 202.

Then, as the motor 20 rotates the substrate 200 for sample analysis, the rotation speed thereof is adjusted (including a case where the rotation is stopped) so that the centrifugal force acting upon the liquid sample in the second channel 206 is less than the capillary force acting upon the liquid sample in the second channel 206.

The second channel 206 is filled by a part of the liquid in the second chamber 202 due to the capillary action. Moreover, as the motor 20 rotates the substrate 200 for sample analysis while the second channel 206 is filled with the liquid, the centrifugal force exceeds the capillary force at a certain point in time. Then, the second channel 206 discharges the liquid from the second chamber 202 into the third chamber 203. As a result, due to the siphon principle, the liquid sample in the second chamber 202 is transferred to the third chamber 203 via the second channel 206. Note that the third chamber 203 is located farther away from the rotation axis P than the second chamber 202, as described above. That is, with respect to the direction in which the centrifugal force is exerted, the third chamber 203 can be said to be located lower (farther) than the second chamber 202. The movement of a liquid through channels as described above will be referred to as the capillary action and the siphon principle. That is, the term "siphon principle" as used herein refers to the transfer being controlled by the balance between the centrifugal force acing upon the liquid due to the rotation of the substrate 10 for sample analysis and the capillary force of the channels. With the provision of a capillary channel and a siphon structure, a liquid can be transferred into a chamber via the channel.

Now, assume an example where an immunoassay is performed using magnetic particles in accordance with the procedure shown in FIG. 17, by using the substrate 200 for sample analysis.

The first chamber 201 is a reaction field where a magnetic particle immobilized antibody 305, an antigen 306 and a labeled antibody 308 are reacted together, eventually producing a complex 310. Therefore, a liquid containing the magnetic particle immobilized antibody 305, an analyte solution containing the antigen 306 and a liquid containing the labeled antibody 308 may be dispensed into the first chamber 201, thereby producing the complex 310.

Alternatively, an immunoassay can be performed in accordance with the procedure shown in FIG. 17 using other chambers and channels. For example, the substrate 200 for sample analysis may include three additional chambers and channels, so that a solution containing the magnetic particle immobilized antibody 305, an analyte solution containing the antigen 306 and a solution containing the labeled antibody 308 are separately held in the three chambers. Each of the chambers is connected to the first chamber 201 via a channel. Then, the liquids are transferred from the three additional chambers to the first chamber 201 via the channels, thereby producing the complex 310.

Alternatively, the magnetic particle immobilized antibody 305 and/or the labeled antibody 308 may be dried (referred to hereinafter as a "dry reagent"), and this dry reagent may be held in the first chamber 201 and dissolved in a liquid containing the antigen 306, thereby producing the complex 310. In such a case, the liquid containing the antigen 306 may be dispensed into the first chamber 201 or may be transferred into the first chamber 201 from another separate chamber via a channel.

Alternatively, dry reagents held in other chambers may be dissolved with a predetermined solution, at the time of measurement, so that liquids containing the antigen 306 are transferred to the first chamber 201 via respective channels to be mixed together in the first chamber 201, thereby producing the complex 310.

Reference is again made to FIG. 16.

The B/F separation is performed in the second chamber 202. The liquid containing the complex 310 in the first chamber 201 is transferred to the second chamber 202 via the first channel 205. The magnetic particles 302 containing the complex 310 are captured onto the wall surface of the second chamber 202 by the magnetic force of the magnet 16a.

The third chamber 203 holds a liquid that is no longer needed in the second chamber 202. The liquid not needed is discharged from the second chamber 202 to the third chamber 203 via the second channel 206.

In the example of FIG. 16, the magnet 16a is arranged at a position in the vicinity of the wall surface of the second chamber 202. This wall surface is a surface perpendicular to the direction in which the centrifugal force is exerted. The centrifugal force is a force exerted in the outward direction as the substrate 200 for sample analysis rotates, and is received by a liquid sample containing the magnetic particles 302. The wall surface of the reaction chamber 14 closer to the magnet 16a supports the liquid sample against the centrifugal force while the substrate 200 for sample analysis is rotating. Note that there is no particular limitation on the position of the magnet 16a as long as magnetic particles can be captured onto the wall surface of the second chamber 202.

Note that if one wishes to use a strict liquid transfer control in the second chamber 202 along the path from the first chamber 201 to the third chamber 203, the second channel 206 described above needs to have a siphon structure, but the first channel 205 does not need to have a siphon structure. Use of a capillary channel and a siphon structure makes it easy to control liquid transfer. FIG. 16 shows an example configuration using the siphon principle. The capillary action and the siphon principle will be described by using an example in which a liquid is transferred from the second chamber 202 to the third chamber 203 shown in FIG. 16. First, as the motor 20 rotates the substrate 200 for sample analysis at a high speed, a liquid sample is transferred from the first chamber 201 to the second chamber 202. The term "rotation at a high speed" as used herein refers to a rotation speed that imposes a centrifugal force greater than a predetermined force on the liquid in the substrate 200 for sample analysis. The term "a rotation speed that imposes a centrifugal force greater than a predetermined force" means a rotation speed such that the rotation of the substrate 200 for sample analysis generates a centrifugal force that prevents a liquid such as a reaction solution from being moved by the gravity, and such that a centrifugal force greater than the capillary force of each capillary channel can be imposed. This similarly applies hereinbelow.

As described above, while the high-speed rotation is maintained, the liquid sample in the second chamber 202 is not transferred to the third chamber 203 via the second channel 206. On the other hand, while the substrate 200 for sample analysis is rotated at a rotation speed such that the centrifugal force is less than the capillary force of the capillary channel (including a case where the rotation is stopped), a part of the liquid in the second chamber 202 fills the second channel 206 due to the capillary action. As the motor 20 rotates the substrate 200 for sample analysis while the second channel 206 is filled with a liquid, the liquid in the second chamber 202 starts to be transferred to the third chamber 203 at a point in time when the centrifugal force exceeds the capillary force. As a result, the liquid sample is continuously transferred from the second chamber 202 to the third chamber 203 due to the siphon principle as long as the motor 20 maintains a rotation speed greater than or equal to this rotation speed.

As described above, the first channel 205 and the second channel 206 are each preferably a capillary channel capable of drawing and transferring a liquid by virtue of the capillary action.

Note however that the first channel 205 and the second channel 206 do not necessarily need to be channels using the capillary action. In view of this, a case will now be described in which a liquid is transferred from the first chamber 201 to the third chamber 203 via the second chamber 202, wherein the transfer of the liquid between the second chamber 202 and the third chamber 203 is controlled.

For example, where the rotational angle position of the substrate 200 for sample analysis is adjusted so as to create a height difference between the first chamber 201 (start) and the second chamber 202 (destination), thereby transferring a liquid sample via the first channel 205 by using the gravity, the substrate 200 for sample analysis is supported with the rotation axis P being in the range of greater than 0° and 90° or less with respect to the vertical direction. The first chamber 201 is shaped so that a liquid can be held in the first chamber 201 at a certain rotational angle position. The first chamber 201 is further shaped so that when the rotational angle of the substrate 200 for sample analysis is changed, the liquid held in the first chamber 201 is allowed to flow into the second chamber 202 via the first channel 205. As a specific example, it is preferred that the outermost wall surface of the first chamber 201 (the wall surface farthest away from the rotation axis P) is depressed so that the outermost wall surface is capable of holding the liquid sample when the substrate 200 for sample analysis is held at a predetermined angle. In such a case, the second channel 206 may be a capillary channel (including a siphon structure) or a channel that is capable of transferring a liquid sample by using the gravity. Note however that where the second channel 206 is a channel that is capable of transferring a liquid sample by using the gravity, the outermost wall surface of the second chamber 202 is preferably depressed, as is the first chamber 201 described above.

On the other hand, it is possible to employ a configuration where the reaction to produce the complex 310 and the B/F separation are performed in the second chamber 202. However, the substrate 200 for sample analysis illustrated in the present embodiment assumes that the reaction to produce the complex 310 is performed in the first chamber 201, not in the second chamber 202. This is because if the reaction to produce the complex 310 is performed in the second chamber 202, the reaction to produce the complex 310 will be performed with the magnetic particles captured by the magnet 16a onto the wall surface of the second chamber 202. That is, if the reaction to produce the complex 310 is performed in the second chamber 202, the reaction to produce the complex 310 will be performed with the positions of the magnetic particles substantially fixed, thereby deteriorating the reaction efficiency and increasing the amount of time required for the complex-producing reaction.

When performing an immunoassay, a luminescent substrate or a chromogenic substrate held in a chamber (not shown) may be transferred to the second chamber 202, after the reaction to produce the complex 310 is complete, thereby causing a luminescent or chromogenic reaction. In order to effectively suppress adsorption onto nonspecific magnetic particles 302, a cleaning liquid held in a chamber (not shown) may be transferred to the second chamber 202, after the reaction to produce the complex 310 is complete, thereby cleaning (and discharging) the magnetic particles 302. Attempting to complete such a step within the substrate 200 for sample analysis, different liquids need to be transferred to the second chamber 202 containing the magnetic particles 302 at predetermined points in time via different chambers and channels provided separately. This requires a complicated rotation control for the substrate 200 for sample analysis. For example, a part of the luminescent substrate or the chromogenic substrate or a part of the cleaning liquid may possibly be transferred into a chamber containing the magnetic particles 302 (e.g., the second chamber 202) at unintended points in time, e.g., during the reaction to produce the complex 310, because of the rotation control for the substrate 200 for sample analysis.

For such a reason, the substrate 200 for sample analysis of the present embodiment separately includes a chamber for producing the complex 310 and a chamber for performing the B/F separation.

In view of the above description, an example of a liquid sample transferring procedure to be performed in the substrate 200 for sample analysis according to the present embodiment will be described referring to FIG. 18A to FIG. 18C. Note that only the operation of producing the complex 310 and the operation of removing unnecessary liquids will be described below, and the luminescent or chromogenic detection configuration will be omitted. It is assumed that the first channel 205 and the second channel 206 to be described here are capillary channels and they both transfer liquids based on the siphon principle described above.

Figure 18A:
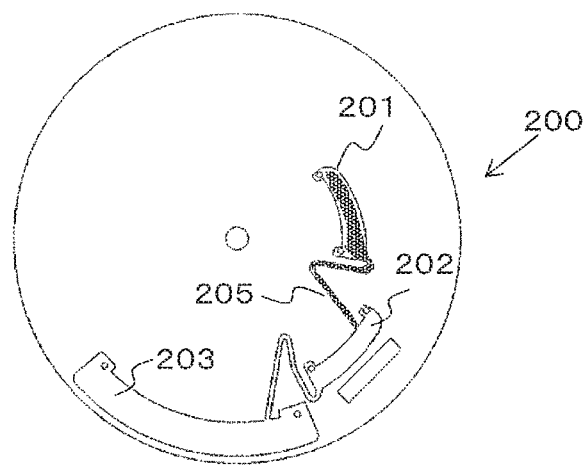
FIG. 18A A view showing an example operation of transferring a liquid in the substrate 200 for sample analysis.
Figure 18B:
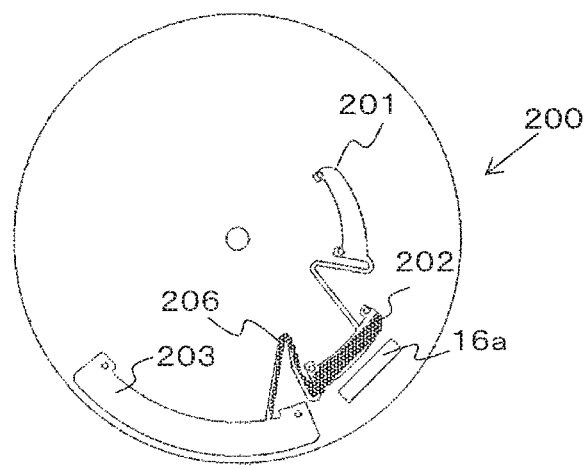
FIG. 18B A view showing the example operation of transferring a liquid in the substrate 200 for sample analysis.
Figure 18C:
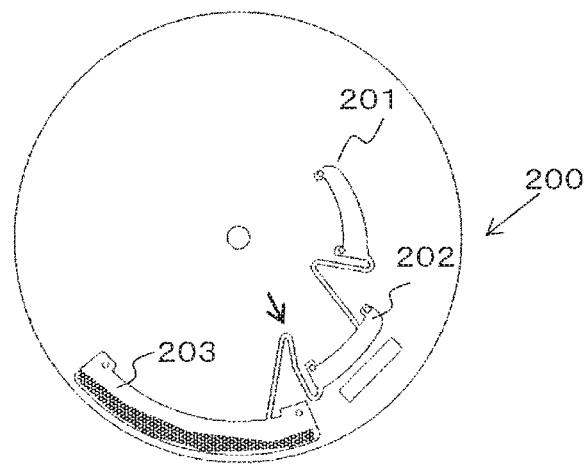
FIG. 18C A view showing the example operation of transferring a liquid in the substrate 200 for sample analysis.

FIG. 18A shows the substrate 200 for sample analysis with a liquid sample introduced into the first chamber 201. In FIG. 18A, a liquid sample is shown by hatching in the first chamber 201.

First, the substrate 200 for sample analysis is set in the sample analysis device 1, and the magnetic particle immobilized antibody 305, an antigen and a labeled antibody are introduced into the first chamber 201. Various introduction methods may be used. For example, the operator may dispense different liquids directly into the first chamber 201, or the liquids may be dispensed into the respective chambers 201 to 203 and transferred to the first chamber 201 as the sample analysis device 1 controls the rotation. Employing any of the introduction methods, the complex 310 will be eventually produced in the first chamber 201. Note that the sample analysis device 1 may allow the complex 310 to be produced, when the substrate 200 for sample analysis is at a halt. However, in order to increase the reaction efficiency and shorten the reaction time, the substrate 200 for sample analysis may be shaken within a predetermined angle range.

When the substrate 200 for sample analysis is at a halt, the liquid sample in the first chamber 201 (also including the magnetic particles 302) is drawn into the first channel 205 by virtue of the capillary action, filling the first channel 205.

Then, the sample analysis device 1 rotates the substrate 200 for sample analysis at a high speed. As a result, the liquid sample in the first chamber 201 undergoes the centrifugal force to be transferred to the second chamber 202 via the first channel 205. FIG. 18B shows the substrate 200 for sample analysis after the liquid sample is transferred from the first chamber 201 to the second chamber 202.

While the substrate 200 for sample analysis is rotating at a high speed, the liquid sample having been transferred to the second chamber 202 will not be transferred to the third chamber 203 via the second channel 206. The magnetic particles 302 in the liquid sample are generally captured by the magnetic force of the magnet 16a onto the wall surface of the second chamber 202. On the other hand, if the rotation of the substrate 200 for sample analysis is stopped, the liquid in the second chamber 202 (which does not substantially contain the magnetic particles 302) is drawn into the second channel 206 by virtue of the capillary action, filling the second channel 206.

Then, the sample analysis device 1 rotates the substrate 200 for sample analysis at a high speed. Thus, the liquid sample in the second chamber 202 of the substrate 200 for sample analysis undergoes the centrifugal force to be transferred to the third chamber 203 via the second channel 206. On the other hand, the magnetic particles 302 remain held in the second chamber 202. FIG. 18C shows the substrate 200 for sample analysis in which the liquid sample, etc., have been transferred to the third chamber 203.

Note that the present embodiment has been directed to an example where the magnet 16a is placed in the substrate 200 for sample analysis. However, other examples are possible. For example, a magnet may be provided in the sample analysis device, not in the substrate for sample analysis.

Figure 19:
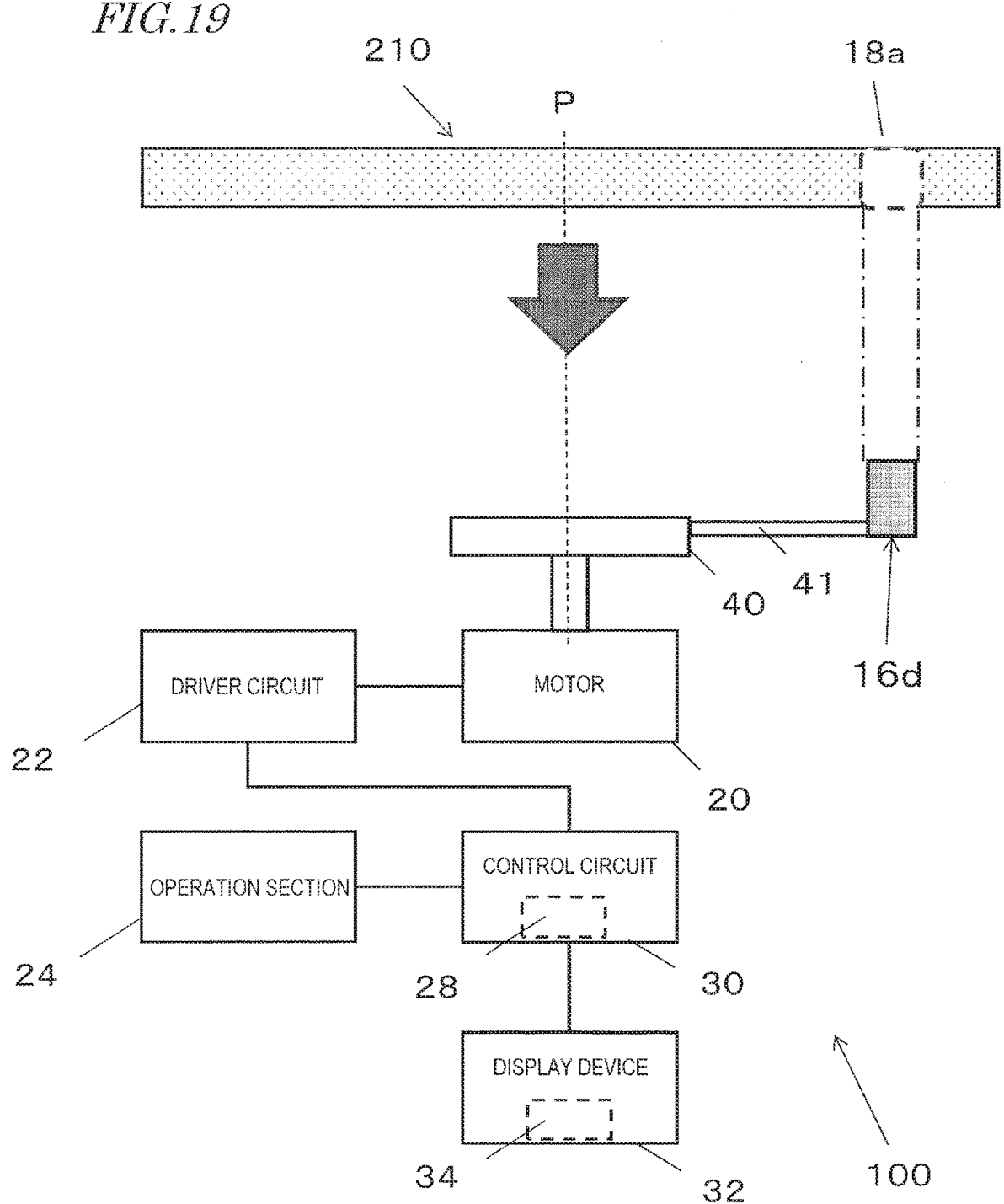
FIG. 19 A diagram showing an example configuration of a sample analysis device 100 having a magnet 16*d*.

FIG. 19 shows a configuration of a sample analysis device 100 according to a variation. Like components to those of the sample analysis device 1 shown in FIG. 3 or the sample analysis device shown in FIG. 5 or FIG. 8 will be denoted by like reference numerals and will not be described below.

The sample analysis device 100 includes an arm 41 mechanically coupled to a bearing 40 having the rotation axis P, with a magnet 16d provided at the tip of the arm 41. A substrate 210 for sample analysis used with this configuration may only need to include the magnet-accommodating chamber 18a into which a magnet is inserted, for example. The opening of the magnet-accommodating chamber 18a may be provided on the upper surface of the substrate 210 for sample analysis or on the lower surface thereof. Alternatively, the opening may be a hole running through the upper surface and the lower surface of the substrate 210 for sample analysis. The position and the size of the magnet 16d are adjusted so that the magnet 16d can be inserted into the magnet-accommodating chamber 18a (FIG. 1B). The magnet-accommodating chamber 18a accommodates the magnet 16d provided in the sample analysis device 100, and also functions as a lock mechanism used when the substrate 210 for sample analysis is rotated by the motor 20 and/or as a torque transmission mechanism.

The internal configuration of the substrate 210 for sample analysis may be the same as those of the substrate 10 for sample analysis and the substrate 200 for sample analysis. That is, also the substrate 210 for sample analysis may only need to include the first chamber 201, the second chamber 202 and the first channel 205, for example.

Note that the sample analysis device 100 described above does not include the magnet detection mechanism 26 (FIG. 3). Since the magnet 16d is inserted every time the substrate 210 for sample analysis is set, there is no need to detect the presence/absence of the magnet. Note that the balancer does not need to be provided on the substrate 210 for sample analysis or provided on the sample analysis device 100.

INDUSTRIAL APPLICABILITY

The present disclosure is applicable to a substrate for sample analysis and a sample analysis device used for analyzing a particular component of an analyte.

REFERENCE SIGNS LIST 1 sample analysis device
10, 110, 200 Substrate for sample analysis
12, 110a Base substrate
14 Reaction chamber
16a Magnet
16b Balancer
16c Fixation boss
18a Magnet-accommodating chamber
18b Balancer-accommodating chamber
18c Fixation hole
20 Motor
22 Driver circuit
24 Operation section
26 Magnet detection mechanism
26a Photodetection device
26b Magnetic force detection device
26c Load detection circuit
28 Signal generation circuit
30 Control circuit
32 Display device
34 Speaker
38 Light source
42 Weight measurement circuit
110b Magnet unit
201 First chamber
202 Second chamber
203 Third chamber
205 First channel
205a First bend
205b Second bend
206 Second channel
302 Magnetic particles
304 Primary antibody
305 Magnetic particle immobilized antibody
306 Antigen 307 Labeling substance
308 Labeled antibody
310 Complex

The invention claimed is:

1. A substrate for sample analysis used for causing a binding reaction between an analyte and a ligand in a liquid sample, the substrate for sample analysis comprising:
   a base substrate having a rotation axis and a predetermined thickness;
   a first chamber located in the base substrate and configured to hold a liquid sample containing an analyte and a ligand immobilized on a surface of magnetic particles;
   at least one magnet arranged at a first position where the magnetic particles are captured in the first chamber by the magnet; and
   a balancer arranged at a second position where, when the at least one magnet is attached, a center of gravity of the substrate generally coincide with the rotation axis, wherein
   the base substrate further includes (1) a second chamber at the first position, and (2) a third chamber at the second position, the second chamber having a first opening in a surface of the base substrate, the third chamber having a second opening in the surface of the base substrate,
   the at least one magnet is removably inserted into the second chamber through the first opening, and
   the balancer is removably inserted into the third chamber through the second opening.

2. The substrate for sample analysis according to claim 1, wherein the first position is a position in the vicinity of a bottom surface of the first chamber.

3. The substrate for sample analysis according to claim 1, wherein:
   the first position is a position in the vicinity of a wall surface of the first chamber of the base substrate; and
   the wall surface is a surface whose normal extends in a direction in which a centrifugal force due to rotation is exerted.

4. The substrate for sample analysis according to claim 1, wherein:
   the first position is a position in the vicinity of a wall surface of the first chamber of the base substrate; and
   the wall surface is a surface on one side where the liquid sample is supported against a centrifugal force due to rotation.

5. The substrate for sample analysis according to claim 1, wherein, the at least one magnet is projecting from the surface of the base substrate when the at least one magnet is being fully inserted into the second chamber.

6. The substrate for sample analysis according to claim 1, wherein:
   the at least one magnet is provided in a magnet unit; and
   the at least one magnet is inserted/extracted to/from the second chamber as the magnet unit is inserted/extracted to/from the base substrate.

7. The substrate for sample analysis according to claim 6, wherein
   the magnet unit is attached at the lower surface so as to be detachable off the surface, and
   the at least one magnet is removably inserted into the second chamber when the magnet unit is attached to the surface.

8. The substrate for sample analysis according to claim 6, wherein the first position is a position in the vicinity of the first chamber.

9. The substrate for sample analysis according to claim 1, wherein the at least one magnet is a plurality of magnets.

10. The substrate for sample analysis according to claim 1, wherein the balancer is a non-magnet.

11. The substrate for sample analysis according to claim 1, wherein
    the balancer is provided fixedly on the base substrate or detachably attached to the base substrate; and
    the at least one magnet is provided fixedly or detachably attached to the base substrate.

12. The substrate for sample analysis according to claim 1, wherein the at least one magnet and the balancer are physically distinguishable from each other.

13. A sample analysis device capable of rotating the substrate for sample analysis according to claim 1, the sample analysis device comprising:
    a motor that rotates the substrate for sample analysis;
    a driver circuit that drives the motor; and
    a detection mechanism that detects whether or not the at least one magnet is attached by using at least one of a weight of the substrate for sample analysis, a magnetic characteristic thereof, an optical characteristic thereof, a current value or a voltage value in accordance with a rotational load thereof, a rotational acceleration thereof and a steady rotation speed thereof.

14. The sample analysis device according to claim 13, further comprising a signal generation circuit that generates a signal notifying of a detection result when the detection mechanism detects that the at least one magnet is not attached.

15. The sample analysis device according to claim 14, wherein the signal generation circuit generates a signal for outputting a sound, light or an image.

* * * * *